(12) United States Patent
Lopez-Ribot

(10) Patent No.: US 7,632,502 B2
(45) Date of Patent: Dec. 15, 2009

(54) **CELL WALL MANNOPROTEINS AND ACTIVE EPITOPES FROM *CANDIDA ALBICANS* AND ANTIBODIES RECOGNIZING THEM**

(75) Inventor: Jose Lopez-Ribot, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 364 days.

(21) Appl. No.: 10/418,303

(22) Filed: Apr. 18, 2003

(65) Prior Publication Data
US 2004/0142385 A1 Jul. 22, 2004

Related U.S. Application Data

(60) Provisional application No. 60/446,560, filed on Feb. 12, 2003, provisional application No. 60/373,324, filed on Apr. 18, 2002.

(51) Int. Cl.
*A61K 39/395* (2006.01)
*A61K 38/16* (2006.01)
*C07K 16/00* (2006.01)
*C12P 21/08* (2006.01)

(52) U.S. Cl. .............. 424/137.1; 424/141.1; 530/387.5; 530/388.1; 530/389.1; 530/388.5; 514/8; 435/975

(58) Field of Classification Search .............. 530/387.5, 530/388.1, 388.5, 389.1; 424/137.1, 141.1; 514/8; 435/975
See application file for complete search history.

(56) References Cited

FOREIGN PATENT DOCUMENTS

WO WO 00/52053 9/2000

OTHER PUBLICATIONS

The Webster's II New Riverside University Dictionary, The Riverside Publishing Company, p. 933, 1984.*
Illustrated Stedman's Medical Dictionary, 24th Edition, Williams & Wilkins, Baltimore, 24th Edition, p. 707, 1982.*
Barturen et al. Microbiology 1535-1543, 1995.*
Bikandi et al. J. Dental Res. 79: 1439-1472, Jun. 2000.*
Casanova et al. Infect. Immun. 60: 4221-4229, 1992.*
Viudes et al., "Identification of Continuous B-Cell Epitopes on the Protein . . . ", Infection and Immunity, May 2001, pp. 2909-2919, vol. 69, No. 5.
Lopez-Ribot et al., "Cloning of a cDNA fragment encoding part of the protein . . . ", FEMS Microbiology Letters 157 (1997), pp. 273-278.
Sentandreu et al., "Cloning and Characterization of PRA1, a Gene Encoding a Novel . . . ", Journal of Bacteriology, Jan. 1998, vol. 180, No. 2, pp. 282-289.

Lopez-Ribot et al., "Comparative Study of the C3d Receptor and 58-Kilodalton . . . ", Infection and Immunity, Jun. 1995, vol. 63, No. 6, pp. 2126-2132.
Sepulveda et al., "*Candida albicans* fibrinogen binding mannoprotein: expression in clinical . . . ", Internatl Microbiol (1998) 1:209-216.
Matthews et al "Antibodies Against *Candida*: Potential Therapeutics?" Sep. 1996, pp. 354-358, vol. 4, No. 9, Trends in Microbiology, Kidlington, Great Britain.
De Bernardis et al "Protective role of antimannan and anti-aspartyl porteinase antibodies in an experimental model of *Candida albican* vaginitis in rats" Aug. 1997, pp. 3399-3405, No. 8, Infection and Immunity.
Monteagudo et al "Tissue invasiveness and non-acidic pH in human candidiasis correlate with "in vitro" expression by *Candida albicans* of the carbohydrate epitope recognized bynew monoclonal antibody 1H4", Jun. 2004, pp. 598-603, vol. 57, No. 6, Journal of Clinical Pathology.
Viudes Angel et al "The C-terminal antibody binding domain of *Candida albican* mp58 represents a protective epitope during candidiasis" Mar. 19, 2004, pp. 133-138, vol. 232, No. 2, FEMS Microbiology Letters.
Cassone et al "Production And Characterization Of A Monoclonal Antibody To A Cell-Surface Glucomannoprotein Constituent Of *Candida-albicans* And Other Pathogenic Candida-Spp", 1988, pp. 233-238, vol. 27, No. 4, Journal of Medical Microbiology.
Yongmoon et al, "Biochemical Characterization Of *Candida albicans* Epitopes That Can Elicit Protective And Nonprotective Antibodies", Oct. 1997, pp. 4100-4107, vol. 65, No. 10, Infection and Immunity, American Society for Microbiology, Washington, US.
Han et al, "Antibody Response That Protects Against Disseminated Candidiasis." Jul. 1995, pp. 2714-2719, vol. 63, No. 7, Infection and Immunity.
Navarro et al, "Diagnosis Of Systemic Candidiasis By Enzyme Immunoassay Detection Of Specific Antibodies To Mycelial Phase Cell Wall And Cytoplasmic Candidal Antigens", 1993, pp. 839-846, vol. 12, No. 11, European Journal of Clinical Microbiology & Infectious Disease, Springer, Wiesbaden, DE.

* cited by examiner

*Primary Examiner*—S. Devi
(74) *Attorney, Agent, or Firm*—Fulbright & Jaworski L.L.P.

(57) ABSTRACT

An isolated surface protein known as mp58 is provided from the yeast *Candida albicans* which has specific active peptide and carbohydrate regions and immunogenic epitopes therein and which elicits strong antibody responses during candidiasis. Antibodies raised from mp58 and the immunogenic regions and epitopes therein are also provided which can recognize the protein and its active regions and epitopes. The protein and antibodies of the present invention will thus be useful in methods of diagnosing, monitoring, treating or preventing infection of *C. albicans* and other yeast, and can also provide the basis for the development of immunity-based prophylactic, therapeutic and diagnostic techniques for the identification and management of disease conditions such as candidiasis.

7 Claims, 13 Drawing Sheets

FIG. 1A
FIG. 1B
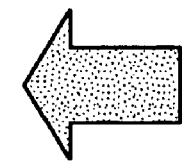 58 kDa

CELL WALL MANNOPROTEINS AND ACTIVE EPITOPES FROM *CANDIDA ALBICANS* AND ANTIBODIES RECOGNIZING THEM

CROSS-REFERENCE TO RELATED APPLICATIONS

The present application claims the benefit of U.S. provisional applications Ser. No. 60/446,560, filed Feb. 12, 2003, and Ser. No. 60/373,324, filed Apr. 18, 2002.

STATEMENT REGARDING FEDERALLY SPONSORED RESEARCH OR DEVELOPMENT

This invention was made with government support under grant number AI42401 awarded by the National Institutes of Health. The government has certain rights in the invention.

FIELD OF THE INVENTION

The present invention relates to the fields of microbiology, molecular biology, and immunology and more particularly relates to surface and cell wall mannoproteins from *Candida albicans* and the epitopic regions therein, including carbohydrate moiety epitopes, the generation of antibodies from said proteins and said epitopes which recognize said epitopes and proteins, as well as the use of said proteins and antibodies to prevent, treat, diagnose, or monitor infections in human and animal patients, such as those caused by different strains of fungi such as those from the genus *Candida*. The invention also relates to vaccines, kits and therapeutic methods based on said proteins and antibodies, and in particular relates to monoclonal antibodies which can recognize the mp58 mannoprotein from *C. albicans* as well as specific epitopes from that protein including the C-terminal region which are immunogenic.

BACKGROUND OF THE INVENTION

*Candida albicans* is the most common fungal pathogen of humans, and the third or fourth most common microorganism isolated from blood cultures obtained in the U.S.A. *C. albicans* is a dimorphic fungus that is both a commensal and opportunistic pathogen of man. Depending on the underlying host defect, *Candida* is able to cause a variety of infections that range from mucosal to life-threatening disseminated candidiasis, having the ability to infect virtually every organ in the host. Predisposing factors for candidiasis include immunosuppressive therapy, massive antibiotic therapy, cytotoxic therapy, intravenous catheters and indwelling devices, very low birth weight, AIDS, diabetes, transplantation medicine, drug dependency, etc. In normal individuals, this organism colonizes the gastrointestinal tract, vagina and some cutaneous areas. Opportunistic superficial and systemic *C. albicans* infections develop in premature newborns, AIDS and debilitated cancer patients, and are particularly frequent and severe after bone marrow transplantation. These opportunistic infections are believed to have an endogenous origin.

One particular condition arising from an infection of *C. albicans* is invasive candidiasis which is a major cause of morbidity and mortality in immunocompromised patients. In general, the morhphogenetic conversions between yeast and hyphal growth forms appear to be critical in the pathogenesis of invasive candidiasis and may be regulated by environmental signals such as extracellular pH. Accordingly, most agree that the ability of *C. albicans* to invade host tissues is largely dependent on the morphogenetic conversions between the yeast and the filamentous forms. Yeast cells and hyphae may encounter different microniches within the host. Besides temperature and serum, extracellular pH is an important environmental cue that regulates the transition between the yeast and the hyphal growth forms.

The extremely severe problems caused by *C. albicans*, including the lack of an early and accurate diagnostic procedure, the high toxicity exhibited by the most common and effective treatments, and the emergence of resistant strains due to empirical prophylactic treatment, have resulted in very high morbidity and mortality rates associated with disseminated infections. Because of these reasons, there is an increasing interest in the development of preventive strategies and in the search for new or alternative therapies to enhance or complement a multicomponent approach to the management of candidiasis. However, despite the efforts of numerous groups of investigators, our present understanding of the pathogenicity mechanisms of this microorganism, as well as our knowledge of factors determining host susceptibility, are still exploratory areas.

As indicated above, pathogenicity resulting from a yeast infection is also dependent on host-related factors. More importantly, the immunological status of the host seems to be of special relevance for susceptibility to fungal and yeast infections. In the case of *C. albicans* and other pathogenic fungi, the importance of cellular defense mechanisms for protection is supported by the fact that most invasive manifestations are detected in patients with deficiencies in cellular immunity. Cell-mediated immunity (T cells) and nonspecific cellular immunity (macrophages, neutrophils and NK cells) are generally believed to play important roles in protection against candidiasis. However, the role of humoral immunity in candidiasis and other fungal infections remains a controversial issue, with contradictory reports that either support or deny the importance of antibody immunity.

In any event, it remains a distinct problem in the field of fungal and yeast infections such as invasive candidiasis to develop adequate means of identifying, treating or preventing such infections so as to control such outbreaks, particularly among highly susceptible patients, such as premature newborns, AIDS sufferers, and debilitated cancer patients In particular, it remains a challenge to develop compositions and methods for treating and preventing fungal infections and diseases such as candidiasis caused by *Candida* microorganisms.

SUMMARY OF THE INVENTION

Accordingly, it is an object of the present invention to provide compositions and method which are useful in the diagnosis, monitoring, treatment or prevention of disease conditions such as candidiasis caused by *Candida* microorganisms.

It is further an object of the present invention to isolate the mp58 mannoprotein from *Candida albicans* and to utilize this protein and the immunogenic epitopes and active regions therein in the development of antibodies which can recognize this protein and/or its epitopes and thus be useful in identifying and/or treating or preventing diseases and infections caused by *Candida* microorganisms.

It is still further an object of the present invention to provide monoclonal antibodies which can recognize the mp58 mannoprotein from *C. albicans* and/or active or epitopic regions therefrom.

It is yet another object of the present invention to provide vaccines, kits and other therapeutic methods which can be utilized in preventing fungal and yeast infections in humans and animals.

These and other objects are provided by virtue of the present invention which comprises an isolated and/or purified surface protein from *Candida albicans*, namely the mp58 mannoprotein, as well as isolated and/or purified peptides or carbohydrates therefrom which contain active or epitopic regions which can be used in immunogenic amounts to generate antibodies capable of recognizing the mp58 mannoprotein and/or those active or epitopic regions. Further, the invention comprises the production of monoclonal antibodies which can recognize the mp58 mannoprotein, or active or epitopic regions therein, including monoclonal antibodies which recognize these proteins and epitopes on a variety of microorganisms from the genus *Candida* and thus are broadly reactive and can be used to diagnose, monitor, treat or prevent a wide variety of infections and other disease conditions caused by *Candida* microorganisms. Finally, the invention also comprises vaccines, kits and other therapeutic and/or immunogenic treatment methods which can be utilized in the diagnosis, monitoring, treatment or prevention of *Candida* infections.

These embodiments and other alternatives and modifications within the spirit and scope of the disclosed invention will become readily apparent to those skilled in the art from reading the present specification and/or the references cited herein, all of which are incorporated by reference.

BRIEF DESCRIPTION OF THE DRAWING FIGURES

FIGS. 1A and 1B illustrate Coomasie (A), Con-A (B), ligand-affinity blot with fibrinogen (C) and immunoblot using PAb anti-mp58 of β-ME cell wall extracts (lanes 1, 2), Zymolyase extracts (lanes 3, 4), and protoplast homogenates (lanes 5, 6) from *C. albicans* yeast cells (lanes 1, 3, 5) and germ-tubes (lanes 2, 4, 6) after separation of the components present in the extracts by SDS-PAGE.

FIG. 2 illustrates the presence of mp58 in the β-ME cell wall extracts from different *C. albicans* clinical isolates as detected by an immunoblot experiment using PAb anti-mp58 as a probe.

FIGS. 3A and 3B illustrate IgG reactivity of serum samples of patients with disseminated candidiasis (n=6) and control individuals (n=5) with the dodecapeptides spanning the entire sequence of the protein portion of mp58. Results represent average and standard deviations. The asterisks denote that statistically significant differences (p<0.05) in the reactivity (candidiasis vs. control) were detected for that particular peptide.

FIG. 5 illustrates serum samples from patients with candidiasis which were tested by ELISA to assess the distribution of IgG subclasses directed against the C-terminal peptide. Although the nature of these experiments did not allow an accurate quantification of the different immunoglobulins subclasses, results indicated that immunoglobulin G (IgG) antibody subclasses were IgG2>IgG1>IgG3>IgG4. Results indicate a mixed Th1/Th2 response, with overall predominance of Th1, which has been correlated with protection against candidiasis (Romani, L. 1999. Immunity to *Candida albicans*: Th1, Th2 cells and beyond. Curr. Opin. Microbiol. 2:363-7).

FIGS. 4A and 4B illustrate the results of an antibody-capture ELISA using the KLH-conjugated C-terminal decapeptide of mp58 for the detection of antibodies present in serum samples from patients with candidiasis and control (non infected) patients. Panel A shows reactivities (expressed as $OD_{490}$ units) as means and standard errors. Panel B shows scattergram of the OD readings for both groups. Reactivities (means and standard errors) of serum samples from patients surviving (good, n=7) or non-surviving (fatal, n=6) disseminated candidiasis are shown in Panel C.

FIGS. 6A-6D illustrate immunoblot analysis used to asses the reactivity of Mab 1H4 with *C. albicans* cell wall materials. Panel A shows reactivity of a rabbit polyclonal antisera containing antibodies against most moieties present in the *C. albicans* β-Me extract, and Panel B shows reactivity of Mab 1H4 against materials present in the cell wall extracts.

FIG. 7 illustrates the effect of periodate oxidation of *C. albicans* mp58 and a *C. albicans* β-ME extract on Mab 1H4 reactivity examined by a modified ELISA assay. Values are expressed as percent reactivity as compared to control (untreated) samples (100%). Error bars indicate standard deviations.

Figure 11A:
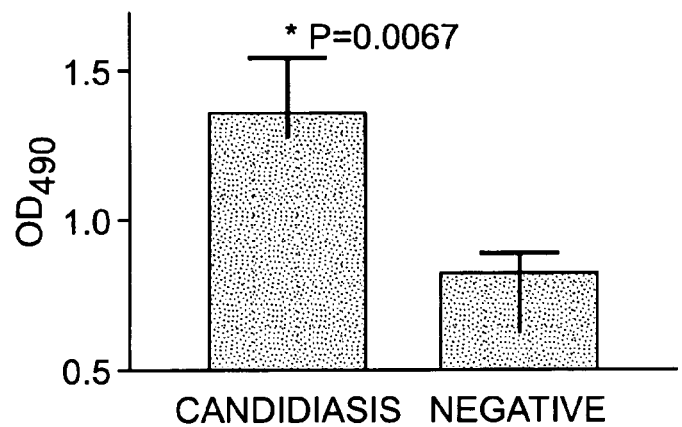
Figure 11B:
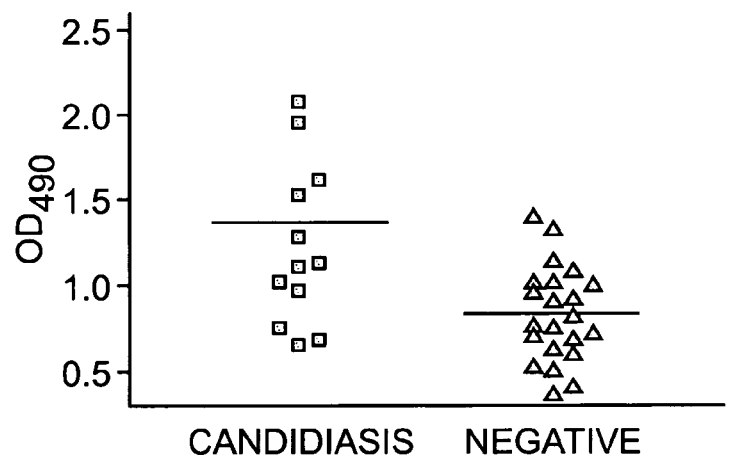
Figure 11C:
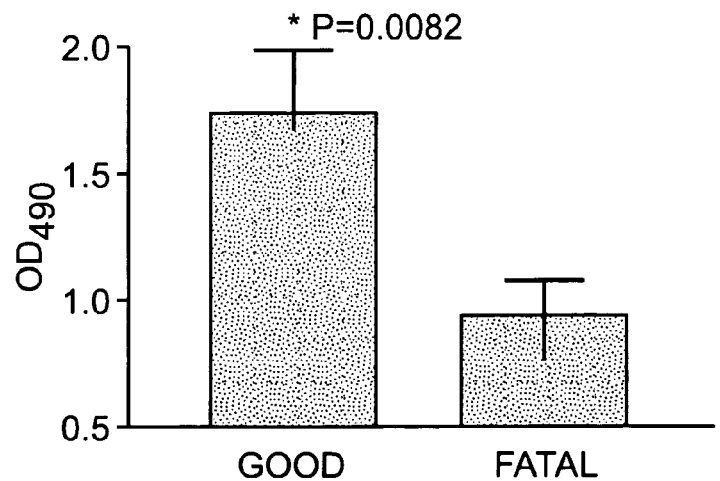

FIGS. 11A-11C illustrate gastric ulcers from patients with invasive candidiasis, obtained at necropsy (A-C) and endoscopic biopsy (D): 1H4-negative yeasts are the predominant form on the superficial part (A and B), with only occasional 1H4-positive mycelial cells (D). Numerous invading mycelial cells showing 1H4 immunoreactivity are seen in the deep part of the ulcers (C). (Immunoperoxidase, hematoxylin counterstain).

Figure 12:
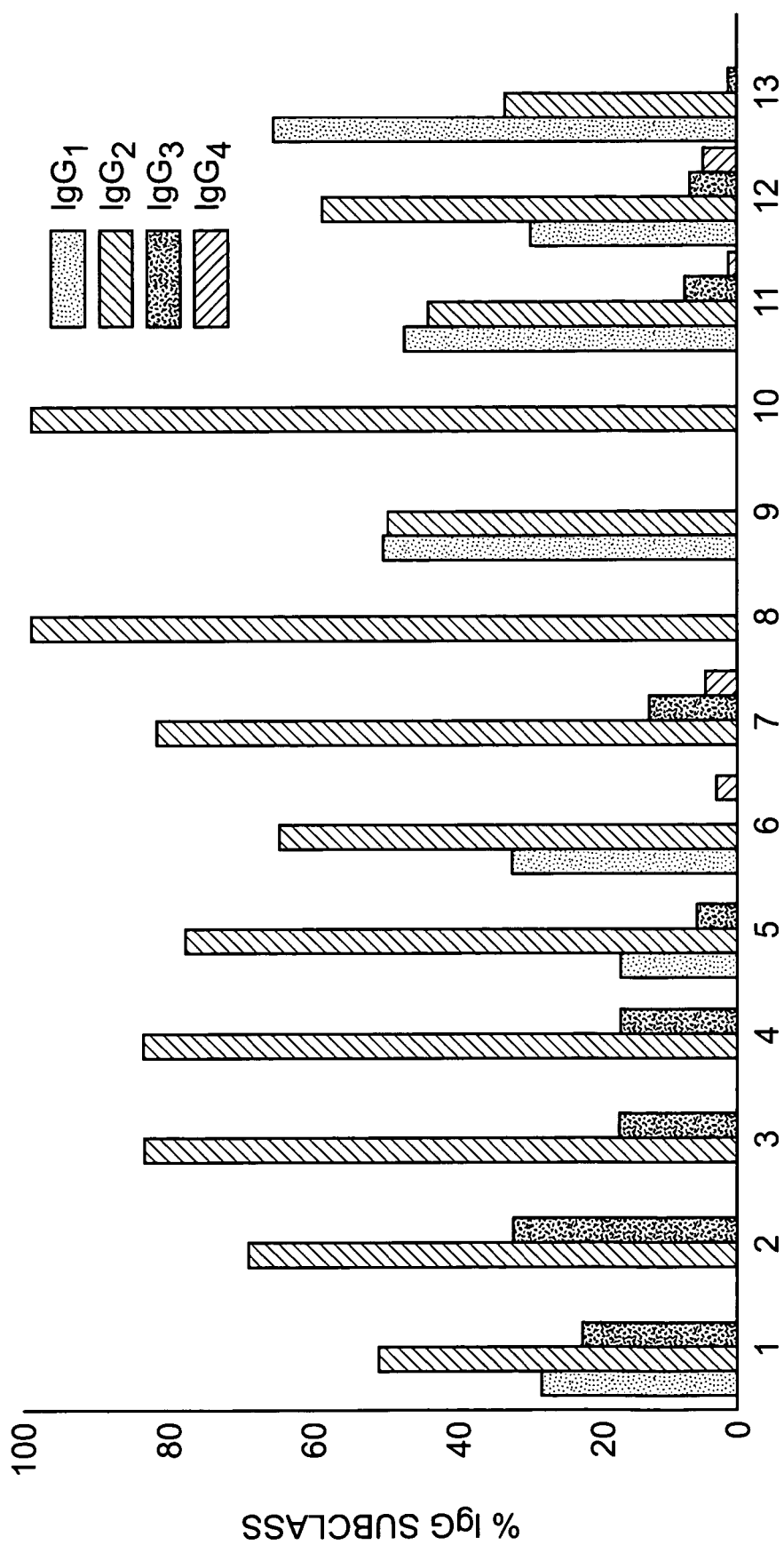

FIG. 12 illustrates 1H4 immunostaining which is detected in fungal remnants within the cytoplasm of tissue macrophages (Immunoperoxidase, hematoxylin counterstain).

Figure 13A:
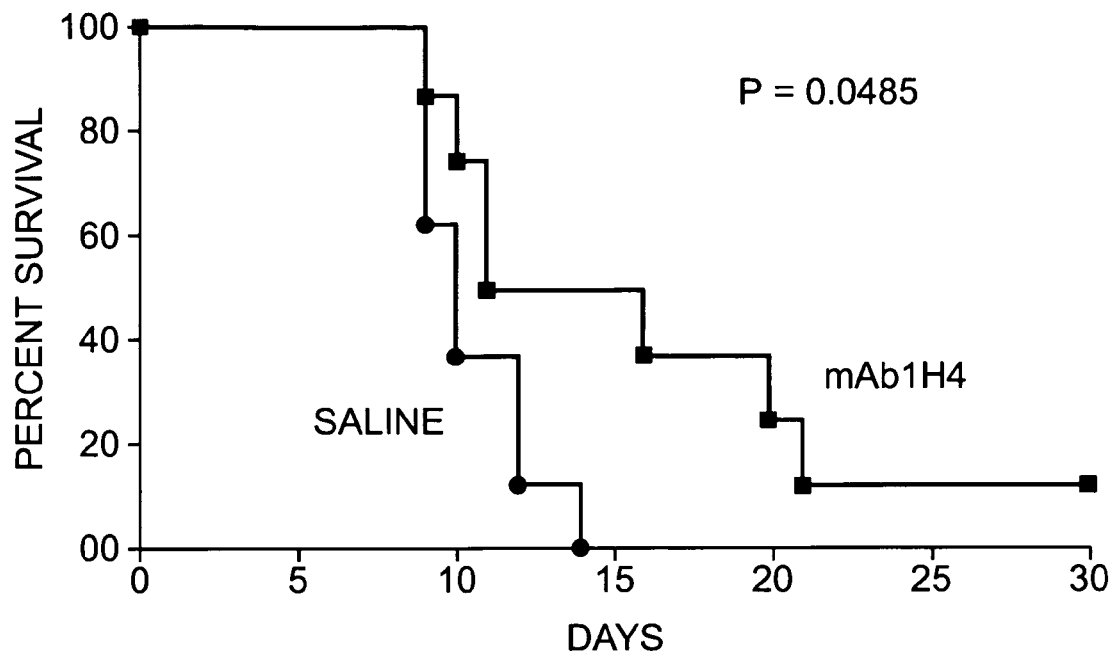
Figure 13B:
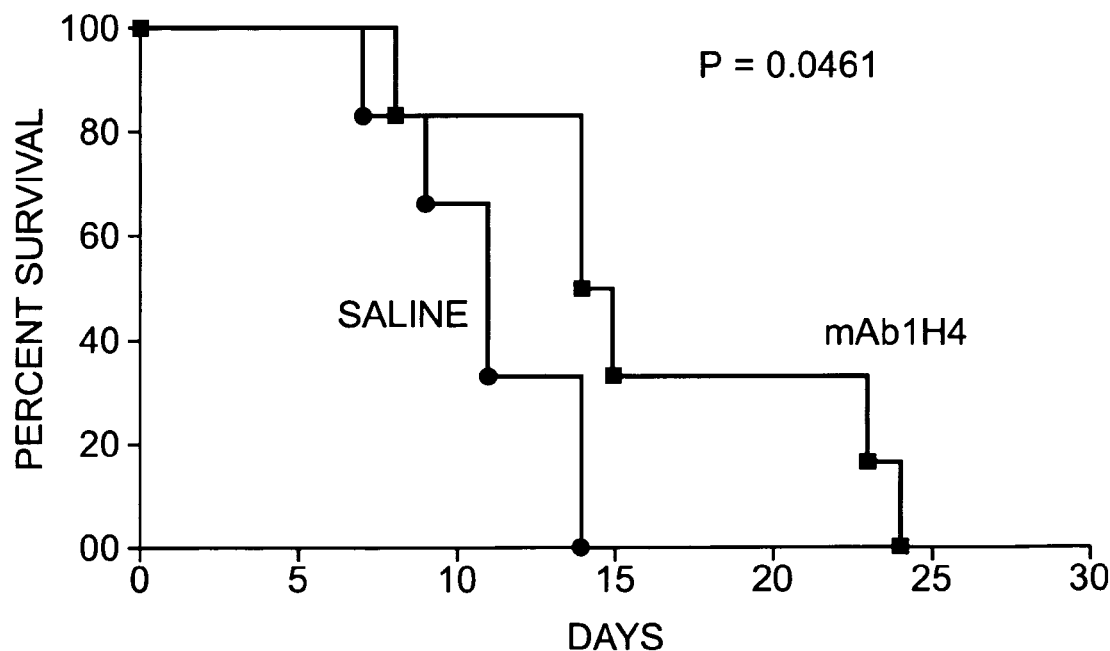

FIGS. 13A and 13B illustrate the passive transfer of protection against *Candida* infection obtainable using the Mab 1H4 in accordance with the present invention. Panel A shows the results of mice who received an intravenous challenge with $1 \times 10^6$ cells of *C. albicans* clinical strain 412 grown overnight in YEPD at 37° C., in Panel B, the intravenous challenge was at 24° C. in Lee medium. Examination of protective effects of Mab 1H4 was performed by monitoring for survival daily after infection (up to 30 days). Survival data and differences between groups were analyzed using the Kaplan-Meier and logrank tests. P<0.05 was considered statistically significant.

DETAILED DESCRIPTION OF THE PREFERRED EMBODIMENTS

In accordance with the present invention, there are provided isolated surface proteins and epitopes from *C. albicans*, namely the cell wall 58-Kilodalton cell wall mannoprotein of *Candida albicans* (mp58) and its active regions and epitopes therein as discussed further below. In addition, we have generated monoclonal antibodies, such as those designated 1H4, 3H3 and 3C2. Tests of mAb 1H4 show that it can recognize pH-sensitive carbohydrate epitopes on the surface of *C. albicans* cells, and that this epitope is not restricted to mp58, but is shared with other cell wall mannoproteins of fungal pathogens. Further tests have shown that mAbs 3H3 and 3C2 recognize the protein portion of mp58.

In accordance with the invention, monoclonal antibody 1H4 was deposited on Apr. 11, 2007 at the American Type Culture Collection, Manassas, Va. 20110-2209 USA, and was accorded Patent Deposit Designation PTA-8325. Monoclonal antibody 3H3 was deposited on Apr. 11, 2007 at the American Type Culture Collection, Manassas, Va. 20110-2209 USA, and was accorded Patent Deposit Designation PTA-8326.

Immunohistological findings indicated that expression of the 1H4 epitope on *C. albicans* cells in tissue sections from human candidiasis correlates with tissue invasion and pH of the niche. Thus, the fact that 1H4 epitope expression selectively identifies invasive and potentially aggressive forms of *Candida albicans* supports its potential value in the management of human candidiasis and in the treatment of or protection against diseases and infections caused by *Candida* microorganisms. In addition, the present invention encompasses other uses of the antibodies of the invention including the preparation of suitable vaccines, the prevention of infection in medical instruments and prosthetic devices, and the provision of kits used to identify an infection by *C. albicans*, all as set forth in further detail herein.

The present invention has focused on the identification and characterization of cell wall proteins and mannoproteins of *C. albicans*, with a special interest in those surface components implicated in adhesion to host cells and tissues. In *C. albicans*, as in several other pathogenic microorganisms, adhesion of the fungus to host cells and tissues is considered to be the initial step leading to establishment of infection, and then hematogenous dissemination can lead to metastatic infection throughout the body. These adhesion processes are mediated by complementary molecules in both the surface of the fungus and the host. In this context, several categories of receptor-like molecules (also designated with the term adhesins) have been identified on the surface of *C. albicans*, including molecules with integrin- and lectin-like activities, along with species in which the sugar moieties (most commonly known as mannan) seem to play an essential role in the interactions. Adhesins described so far include a molecule that presented cross-reactivity towards an antisera raised against the integrin β$_1$ subunit, receptors for complement fragments iC3b and C3d, different serum proteins and a number of extracellular matrix (ECM) components such as laminin, fibronectin, collagens, entactin and vitronectin; moieties that mediate binding to plastic and which are responsible for cell surface hydrophobicity; a unique adhesion system involving mannan moieties by which the fungus binds to macrophages in spleen and lymph-node; fimbrial adhesins; and an extracellular adhesin which mediates attachment to epithelial cells. This repertoire of adhesins displayed by *Candida* is probably a reflection of the range of sites that it can invade in the host, and contribution of the different receptor-like molecules to adhesion may be different depending on the type of cell or tissue in consideration, whether it is an epithelial cell, normal endothelium or exposed extracellular matrix.

As described herein, we have identified, characterized, and cloned a 58 kDa fibrinogen-binding mannoprotein (mp58) on the surface of *C. albicans*, and raised antibodies against the purified component. The mp58 appears to be a major component in β-mercaptoethanol (β-ME) cell wall extracts of both morphological phases of the fungus. It is both N- and O-glycosylated. Confocal microscopy studies revealed that the mp58 is heterogeneously distributed along the surface of the fungus. It is different from other surface adhesins such as laminin receptors, entactin receptors, and receptors binding complement factors, and it is highly hydrophobic. The mp58 is expressed in all *C. albicans* strains tested, including collection strains and fresh clinical isolates. Moreover, it is expressed in fungal cells infecting tissues in patients. Sera from patients suffering from disseminated candidiasis but not from those suffering from superficial forms of the disease and control (normal) individuals contain antibodies against mp58. These observations have evidenced an active role for mp58 during the interaction between *C. albicans* and the host and also reflect the importance of mp58 and antibodies generated therefrom in diagnosing, monitoring, treating or preventing a wide variety of infectious conditions caused by *Candida* microorganisms.

Accordingly, in one particular embodiment of the invention, an isolated and/or purified 58 kilodalton cell wall mannoprotein from *C. albicans* is provided, which has been identified as mp58, along with active regions and other epitopes as described herein which are immunogenic and which can thus be used in generating antibodies capable of recognizing mp58 and/or its active regions and epitopes. The cell wall mannoprotein mp58 has been previously identified and has an amino acid sequence (as set forth in GenBank) as follows:

```
MP58 Amino Acid Sequence                              (SEQ ID NO: 2)

MNYLLFCLFF  AFSVAAPVTV  TRFVNASPTG  YDWRADWVKG  FPIDSSCNAT

QYNQLSTGLQ  EAQLLAEHAR  DHTLRFGSKS  PFFRKYFGND  TASAEVVGHF

ENVVGADKSS  ILFLCDDLDD  KCKNDGWAGY  WRGSNHSDQT  IICDLSFVTR

RYLSQLCSGG  YTVSKSKTNI  FWAGDLLHRF  WHLKSIGQLV  IEHYADTYEE

VLELAQENST  YAVRNSNSLI  YYALDVYAYD  VTIPGEGCNG  DGTSYKKSDF

SSFEDSDSGS  DSGASSTASS  SHQHTDSNPS  ATTDANSHCH  THADGEVHC
```

In addition, the nucleic acid sequences encoding this protein are known and available through GenBank, and said sequences, or degenerative sequences therefrom, will code for mp58 and form part of the present invention. The nucleic acid sequence coding for this protein is derived from a gene sequence of 1596 nucleotides having the following sequence wherein the coding regions is from bases 569 to 1468 of the sequence:

PRA1 gene (SEQ ID NO: 1)

```
   1 acagtttctg tataaacctt agtcaataac ccgatgaaaa taaatgggta aaccttcatt
  61 gatgttgtta attttagag agctaccacc aaaaacatat tcagcaaagg ctacctttat
 121 attaattatt ccgttttcca agattcctag cggtcgccaa gagaactcaa cactttaacc
 181 accatggtat atatcttcat tgctacgggc ccatatattc atgtttccaa ctattctggg
 241 caacctcatt ttgtccaaca attttggtga acagttaaaa ttttgcatga aatctttcgc
 301 acccacgcac tctcatcaca accactacag ttctatttgc aagagatac cagatgcaag
 361 taattaatat attattttct cggtatcttc atggatcagt attccgaaca attcaagaaa
 421 agaaagaagg agcgggaaca gttataatgg ttatatctta tgtgttaacc aaagtataaa
 481 gaggcaacaa tatctcgttg gaaaagacct ttgtttggtt aatcattttt tttattcaca
 541 tctataatca caaactttct ctcgaaatat gaattattta ttgttttgtt tattttttgc
 601 tttttccgtt gctgcaccag ttacggttac cagatttgtt aatgcttcac ctacaggtta
 661 cgattggcgg gccgactggg ttaaaggttt tccgattgat ctgtcgtgta atgccacaca
 721 atataatcaa ttatctactg ggttgcaaga agctcaatta ttagctgaac atgccagaga
 781 ccacacattg agattcggta gcaaatcgcc attttcaga aaatactttg gaaatgacac
 841 tgcaagtgct gaggtcgttg gtcattttga aaatgttgtc ggtgctgaca aatcatccat
 901 tttgtttctt tgtgatgact tagatgataa gtgcaaaaat gatggctggg ctggctattg
 961 gagaggttcc aaccatagtg atcaaactat tatttgtgac ttatcttttg ttaccagaag
1021 atacttatcc caactatgct ccggtggata taccgtctcg aaatctaaga caaacatttt
1081 ttgggcaggt gacttgttac acagattctg gcacttgaaa tcgattggtc aacttgttat
1141 tgaacattac gctgacactt atgaggaggt tcttgaattg gctcaagaaa attcaactta
1201 tgctgtaaga aactcaaact cattgattta ttatgctttg gatgtgtatg catatgatgt
1261 gacaattccc ggcgaagggt gcaatggaga tggtactctg tacaagaaat cagattttag
1321 cagcttcgag gatagcgaca gtggctctga ttcaggggcc agtagcacag cctcaagttc
1381 tcatcaacat accgatagca acccctagcgc cacaacagat gctaacctgc attgccacac
1441 acatgcagat ggtgaagtcc actgttaatt gttaagttca ggcattaaac aatttttaag
1501 gtgtttcatg gatatctttt tatagattga attaataaga ttaattgcaa aatcgcttgt
1561 agacaaaaga gtaatttta tctaaatcta gaattg
```

The coding region for mp58 is thus the following nucleic acid sequence of 900 nucleotides, and the invention contemplates that this sequence will also have equivalent degenerative sequences which also code for the mp58 mannoprotein, or the peptides and epitopes disclosed herein, as would be recognized by one skilled in this art:

MP58 Nucleic Acid Sequence (SEQ ID NO: 3)

```
   1 atgaattatt tattgttttg tttatttttt gcttttccg ttgctgcacc agttacggtt
  61 accagatttg ttaatgcttc acctacaggt tacgattggc gggccgactg ggttaaaggt
 121 tttccgattg atctgtcgtg taatgccaca caatataatc aattatctac tgggttgcaa
 181 gaagctcaat tattagctga acatgccaga gaccacacat tgagattcgg tagcaaatcg
 241 ccattttca gaaaatactt tggaaatgac actgcaagtg ctgaggtcgt tggtcatttt
 301 gaaaatgttg tcggtgctga caaatcatcc attttgtttc tttgtgatga cttagatgat
 361 aagtgcaaaa atgatggctg ggctggctat tggagaggtt ccaaccatag tgatcaaact
```

```
                          -continued
421 attatttgtg  acttatcttt  tgttaccaga  agatacttat  cccaactatg  ctccggtgga 481 tataccgtct  cgaaatcaa   gacaaacatt  ttttgggcag  gtgacttgtt  acacagattc 541 tggcacttga  aatcgattgg  tcaacttgtt  attgaacatt  acgctgacac  ttatgaggag 601 gttcttgaat  tggctcaaga  aaattcaact  tatgctgtaa  gaaactcaaa  ctcattgatt 661 tattatgctt  tggatgtgta  tgcatatgat  gtgacaattc  ccggcgaagg  gtgcaatgga 721 gatggtactc  tgtacaagaa  atcagatttt  agcagcttcg  aggatagcga  cagtggctct 781 gattcagggg  ccagtagcac  agcctcaagt  tctcatcaac  ataccgatag  caaccctagc 841 gccacaacag  atgctaacct  gcattgccac  acacatgcag  atggtgaagt  ccactgttaa
```

The 58-kilodalton mannoprotein (mp58) on the surface of *Candida albicans* is highly immunogenic, is expressed by all *C. albicans* isolates tested, and elicits strong antibody responses during candidiasis. It belongs to a family of immunodominant fungal antigens with homologs also in different species of *Aspergillus*. In accordance with the present invention, the amino acid sequence of the protein portion of mp58 as deduced from the DNA sequence of its encoding gene (FBP1/PRA1), and as set forth above, was used to synthesize a complete set of overlapping dodecapeptides (overlap, 7; offset, 5) which were covalently attached to the surface of derivatized polyethylene pins. The pin-coupled peptides were used in a modified enzyme-linked immunosorbent assay (ELISA) to identify continuous epitopes recognized by a number of antiserum preparations containing anti-mp58 antibodies. This comprehensive epitope-scanning study revealed the presence of multiple immunoreactive continuous B-cell epitopes within the protein sequence. Regions of increased reactivity included both the amino and carboxy termini of the mature protein (encompassing amino acid residues 16 to 50 (SEQ ID NO:4) and 286 to 299 (SEQ ID NO:5), respectively) and four internal regions spanning amino acids at positions 66 to 92 (SEQ ID NO:6), 121 to 142 (SEQ ID NO: 7), 148 to 192 (SEQ ID NO:8), and 211 to 232 (SEQ ID NO:9).

Further delineation of epitopic regions and identification of the boundaries of the antigenic sites was performed upon ELISA testing with a second Pepset consisting of completely overlapping 8-mer peptides spanning these reactive regions in the protein moiety of mp58. The highly reactive epitopic region at the C terminus of the protein was further evaluated using both window net and replacement net analyses. A synthetic peptide corresponding to the last 10 amino acid residues at the C terminus of the protein was immunogenic when injected into mice after being coupled to a carrier protein. Moreover, antibodies in the resulting sera specifically recognized the homologous mp58 in ELISAs and immunoblot assays, and thus these antibodies and the immunological responses to mp58 will be useful in the development of immunity-based prophylactic, therapeutic, and diagnostic or monitoring techniques for the management of candidiasis, as described hereinbelow.

In particular, the present invention contemplates the generation of antibodies from the mp58 mannoprotein as well as its epitopes and peptides comprising the active regions as set forth above. By "antibody" is meant any intact antibody molecule or fragments thereof that recognize antigen (e.g. Fab or F(ab')2 fragments) and can be of polyclonal or monoclonal type, and the antibodies in accordance with the invention will be capable of recognizing the mp58 mannoprotein and/or the specific epitopes which will be common in a variety of *Candida* microorganisms and will thus be effective in methods of diagnosing, monitoring, treating or preventing infection from *Candida*. By "epitope" is meant any antigenic determinant responsible for immunochemical binding with an antibody molecule. Epitopes usually reside within chemically active surface groupings of protein molecules (including amino acids and often also sugar side-chains) and have specific three-dimensional structural characteristics and specific charge characteristics. With reference to the mp58 mannoprotein, or its epitopes and peptides as described herein, it is understood that such terms also include those proteins and peptides which differs from a naturally occurring or recombinant protein by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end.

For example, a synthetic peptide corresponding to the last ten amino acid residues at the C-terminus of the protein ($^{290}$HTHADGEVHC$^{298}$) (SEQ ID NO: 10) was immunogenic when injected to two mice after coupling to a carrier protein. Moreover, the resulting sera specifically recognized the homologous mp58 in ELISA and immunoblot assays. Initial experiments were directed to optimize an synthetic peptide-based antibody-capture assay to examine presence of antibodies against this mimetic sequence in human serum samples. The following parameters of the antibody-capture ELISA were assessed: i) use of free peptides as compared to the use of KLH-conjugated peptides as materials for coating the wells, iii) use of different quantities of peptide for coating the wells of microtiter plates, iii) use of different types of ELISA plates for optimal adsorption of synthetic peptides, including different types of plastics and chemistry-modified plates, iv) use of different coating buffers, v) use of different blocking reagents including protein and detergents and vi) use of different dilutions of sera. In its final format the KLH-conjugated peptide was used to coat Immulon 2 plates in a carbonate buffer (pH 9.6) at a concentration of 1µg/well, after overnight incubation at 4° C. and washes with PBS the different serum samples from patients with candidiasis (1:1,000 dilution in PBS with 0.05% TWEEN 20® [PBST] and 1% BSA) were added to the wells and incubated for 1 h at 37° C. Then the plates were washed with PBST and incubated with peroxidase-conjugated goat-anti human IgG (1:2,000 dilution) for 1 h at 37° C. After washings, plates were developed (OPD in citrate buffer) and read at 490 nm in a microtiter plate reader. Once the assay was optimized, a larger number of serum samples from patients with disseminated candidiasis (n=13) and control individuals (n=22) were tested.

Figure 4A:
Figure 4B:
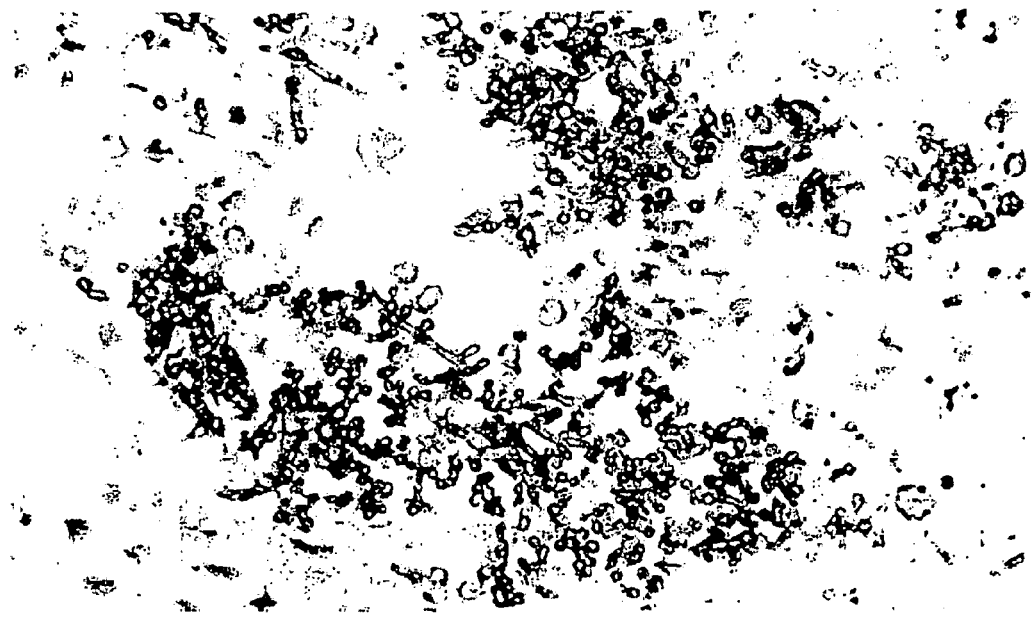

These experiments confirmed the increased levels of antibodies against this peptide in serum samples from patients with disseminated candidiasis as compared to control individuals (FIG. 4, panels A and B). Moreover, levels of anti-peptide antibodies were significantly higher in surviving patients compared to those with fatal outcomes (FIG. 4, Panel C) thus indicating that this peptide represents a protective epitope during candidiasis in accordance with the present invention. In addition, levels of reactivity against C. albicans cytosolic and β-ME extracts of antibodies in sera from good and fatal outcome were similar, so higher levels of reactivity against the C-terminal peptide illustrated the immunogenic properties of this peptide and were not due to overall higher antibody levels in survivor vs. those who succumbed to the infection.

Similarly, tests were performed to determine the ability of antibodies generated in accordance with the invention, as described further below, to recognize active regions and/or other epitopes of the mp58 mannoprotein in addition to recognizing the mp58 mannoprotein itself. In these tests, Immulon 2-HB high-binding 96-well microtiter plates (Dynex) were coated with 1 μg/well of β-ME cell wall extract of C. albicans strains 10261, 26555 or mp58 C-terminal peptide (HTHADGEVH) (SEQ ID NO: 11) in 1× PBS, pH 7.4 and incubated for 2 hours at room temperature. All washing steps in ELISAs were performed three times with 1× PBS 0.05% TWEEN 20® wash buffer. Plates were washed and blocked with a 1% BSA solution at room temperature for 1 hour before hybridoma supernatant samples were added to wells. Plates were incubated with samples and relevant controls such as media alone for one hour at room temperature, washed, and goat anti-mouse IgG-AP (Sigma) diluted 1:5000 in 1× PBS, 0.05% TWEEN 20®, 0.1% BSA was used as a secondary reagent. Plates were developed by addition of 1 mg/ml solution of 4-nitrophenyl phosphate (pNPP) (Sigma), followed by incubation at 37° C. for 30 minutes. Absorbance was read at 405 nm using a SPECTRAMAX® 190 Plate Reader (Molecular Devices Corp.). Antibody supernatants that had an $OD_{405} \geq 3$ times above background (media alone, ~0.1 OD) were considered positive. The results from these tests indicate that the mp58 monoclonal antibodies identified as 3H3 and 3C2 mAbs recognize native mp58 expressed in the cell wall of Candida albicans as well as a synthetic non-apeptide derived from the sequence of the C-terminus of mp58 (amino acids HTHADGEVH) (SEQ ID NO:11).

In accordance with the present invention, isolated and/or purified mp58-recognizing antibodies can be generated from the mp58 mannoprotein from C. albicans or from one or more of the active regions of this protein as described above, or from particular epitopes such as those epitopic peptide sequences from the C terminal region as also described above. These antibodies may be monoclonal or polyclonal and may be generated using any suitable method to raise such antibodies such as would be well known in this art.

For example, with regard to polyclonal antibodies, these may be generated using a number of suitable methods generally involving the injection of the isolated and/or purified or recombinantly produced mp58 (or its immunogenic active peptides or epitopes) into a suitable host in order to generate the polyclonal antibodies which can then be recovered from the host. In one specific example in accordance with the invention, purified mp58 was injected to rabbits to generate polyclonal antisera against this component (PAb anti-mp58). When this polyclonal antiserum was used in immunoblot and IIF techniques, the recognition patterns were basically identical to those detected for fibrinogen binding.

In addition, monoclonal antibodies in accordance with the invention may be generated using a suitable hybridoma as would be readily understood by those of ordinary skill in the art. In the preferred process, the mp58 mannoprotein from C. albicans is first isolated and/or purified in a number of suitable ways, or produced by recombinant means as would be commonly used in the art. In one suitable purification process, the proteins of the cell wall have been isolated and examined using polyacrylamide gel electrophoresis (PAGE) and Western-blot techniques. In the preferred process, a combination of chemical (β-ME) and enzymatic (Zymolyase) solubilization techniques are used to release the genuine cell wall components from intact cells of C. albicans. Treatment of both yeast cells and germ tubes of C. albicans with β-ME leads to solubilization of a complex array of proteins and mannoproteins. Ligand affinity blotting with a combination of fibrinogen and anti-fibrinogen antibody allowed detection of a 58 kDa component (mp58) in extracts from both fungal morphologies which specifically interacts with human fibrinogen. The mp58 is a mannoprotein as indicated by its reactivity against Concanavalin A (ConA). Also, it is highly hydrophobic as determined for its ability to bind polystyrene-latex microbeads. Strong fluorescence was observed when C. albicans germ tubes were incubated in the presence of fibrinogen in an indirect immunofluorescence experiment. The mp58 was purified and the purified preparation was then used to generate antibodies in accordance with the invention.

In one suitable process, monoclonal antibodies were generated by isolating mp58 as described above followed by purification steps. For purification of mp58, components in the βME were separated by preparative sodium dodecyl sulfate-polyacrylamide gel electrophoresis (SDS-PAGE) under denaturing conditions as described by Laemmli. The transverse sections of the gels corresponding to mp58 (as identified by Coomassie staining) were excised, crushed and the polypeptide moieties electroeluted. A second process for generating recombinant mp58 involves the cloning and expressing of mp58 in S. cerevisiae. Briefly, mp58 DNA was cloned by PCR into pYES2/CT as C' fusion to V5 and His tags or into pYES2/NT as N' fusion to Xpress and His tags. The plasmids were transformed into YPH499 and selected on SD-URA plate. The mp58 fusion is under the control of GAL1 promoter, and the expression is induced by galactose. Three methods were used to extract mp58 from the yeast cells; a). yeast cells were broken with glass beads by vortex in yeast extraction buffer containing 1× PBS (7.4), 1 mM EDTA, 1 mM DTT, 0.5% TRITON X-100®, 5% glycerol, 1 mM PMSF, 1× PIC (Sigma), b). yeast cells were resuspended in 1× PBS (7.4), 1% SDS, 1% β-ME and heated to near boiling for 30 min, and c). yeast cells were treated in 1× PBS (7.4) containing 2.5 mg/ml of ZYMOLYASE 20-T® for 3 hrs at 37° C. The expression of mp58 fusion protein was detected by both anti-His antibody and mAb 3C2. The recombinant his-tagged mp58 was purified by metal chelating chromatography.

To generate the monoclonals, pure mp58 was mixed with adjuvant, and injected to BALB/c mice. Immunization protocols consisted of a first injection (using complete Freund's adjuvant), two subsequent booster injections (with incomplete Freund's adjuvant) at three-week intervals, and one final booster injection without adjuvant three days prior to fusion (all injections were subcutaneous). For hybridoma production, mice were sacrificed and their spleen removed aseptically. Antibody secreting cells isolated and mixed with myeloma cells (NS1) using drop-wise addition of polyethylene glycol. After the fusion, cells were diluted in selective medium (vitamin-supplemented DMEM/HAT) and plated at low densities in multiwell tissue culture dishes. Tissue supernatants from the resulting fusion were screened by both ELISA (using the total 2-ME extract to coat the wells of a microtiter plate) and immunoblot techniques. Cells from these positive wells were grown and single cell cloned by limiting dilution, and supernatants subjected to one more round of screening by both ELISA and immunoblot. Positive clones were identified, and monoclonal antibodies collected as hybridoma supernatants, including 3H3, which is an IgG1.

Determination of the epitope recognized by Mab 3H3 was performed by means of the Multipin Peptide Technology (see above) demonstrated that this Mab recognized the C-terminal epitope previously identified as highly reactive by using polyclonal antisera preparations. (Viudes et al, I & I 2001). Further delineation of the epitope recognized by Mab 3H3 was performed using window-net and replacement-net approaches. The window-net analysis identified the nonapeptide $^{290}$HTHADGEVH$^{298}$. (SEQ ID NO: 11) as the minimal region that retained most of the antibody-binding activity for Mab 3H3. The replacement net analysis revealed the important role of the histidines (residues 290, 292 and 298) in the recognition by antibodies, since single substitutions of each of these histidine residues resulted in abrupt decrease in levels of reactivity.

In accordance with the invention, antibodies are thus produced which are generated from mp58 and/or its active regions and epitopes contained therein, and such antibodies are capable of recognizing and binding mp58 and/or its epitopes and active regions and can be utilized in many diagnostic and therapeutic applications such as the ones described in more detail below.

Vaccines, Humanized Antibodies and Adjuvants

The isolated antibodies of the present invention, or the isolated proteins or epitopes as described above, may also be utilized in the development of vaccines for active and passive immunization against yeast and fungal infections, as described further below. In the case of active vaccines, said vaccines are prepared by providing an immunogenic amount of the mp58 mannoprotein or the active regions or epitopes as set forth above, and the active vaccine in accordance with the invention will thus comprise an immunogenic amount of the protein or peptide and will be administered to a human or animal in need of such a vaccine. The vaccine may also comprise a suitable, pharmaceutically acceptable vehicle, excipient or carrier such as described above. As referred to above, an "immunogenic amount" of the antigen to be used in accordance with the invention is intended to mean a nontoxic but sufficient amount of the agent, such that an immunogenic response will be elicited in the host so that the desired prophylactic or therapeutic effect is produced. Accordingly, the exact amount of the antigen that is required will vary from subject to subject, depending on the species, age, and general condition of the subject, the severity of the condition being treated, the particular carrier or adjuvant being used and its mode of administration, and the like. Similarly, the "immunogenic amount" of any such antigenic vaccine composition will vary based on the particular circumstances, and an appropriate immunogenic amount may be determined in each case of application by one of ordinary skill in the art using only routine experimentation. The dose should be adjusted to suit the individual to whom the composition is administered and will vary with age, weight and metabolism of the individual.

Further, when administered as pharmaceutical composition to a patient or used to coat medical devices or polymeric biomaterials in vitro and in vivo, the antibodies of the present invention may also be useful because these antibodies may be able to interfere with the ability of fungi and yeast to adhere to host cells and limit the extent and spread of the infection.

In addition, the antibody may be modified as necessary so that, in certain instances, it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., Nature 321:522-525 (1986) or Tempest et al. Biotechnology 9:266-273 (1991) or "veneered" by changing the surface exposed murine framework residues in the immunoglobulin variable regions to mimic a homologous human framework counterpart as described, e.g., by Padlan, Molecular Imm. 28:489498 (1991), these references incorporated herein by reference. Even further, when so desired, the monoclonal antibodies of the present invention may be administered in conjunction with a suitable antibiotic to further enhance the ability of the present compositions to fight fungal infections.

In a preferred embodiment, the antibodies may also be used as a passive vaccine which will be useful in providing suitable antibodies to treat or prevent a yeast or fungal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the fungal infection to be dealt with and the condition of the patient. The vaccine is preferably combined with a pharmaceutically acceptable vehicle, carrier or excipient to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a fungal infection, and one would readily recognize that this amount will vary greatly depending on the nature of the infection and the condition of a patient. An "effective amount" of antibody or pharmaceutical agent to be used in accordance with the invention is intended to mean a nontoxic but sufficient amount of the agent, such that the desired prophylactic or therapeutic effect is produced. Accordingly, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

In addition, the antibody compositions of the present invention and the vaccines as described above may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

Pharmaceutical Compositions

As would be recognized by one skilled in the art, the antibodies of the present invention may also be formed into suitable pharmaceutical compositions for administration to a human or animal patient in order to treat or prevent a yeast or fungal infection, such as those caused by *Candida* species microorganisms. Pharmaceutical compositions containing the antibodies of the present invention as defined and described above may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of antibody compositions, and other information concerning compositions, methods and applications with regard to other microbial surface proteins and peptides will generally also be applicable to the present invention involving monoclonal antibodies and are disclosed, for example, in U.S. Pat. No. 6,288,214 (Hook et al.), incorporated herein by reference.

The antibody compositions which are generated in accordance with the present invention may also be administered with a suitable adjuvant in an amount effective to enhance the immunogenic response against yeast. For example, suitable adjuvants may include alum (aluminum phosphate or aluminum hydroxide), which is used widely in humans, and other adjuvants such as saponin and its purified component Quil A, Freund's complete adjuvant, RIBI adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147: 410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

In any event, the antibody compositions of the present invention will thus be useful for interfering with, modulating, or inhibiting binding interactions by yeast and other fungi. Accordingly, the present invention will have particular applicability in developing compositions and methods of preventing or treating yeast and fungal infections, and in inhibiting binding and spreading of yeast and fungi to host cells.

Methods:

Detecting and Diagnosing Infections Caused by *Candida* Microorganisms

In accordance with the present invention, methods are provided for identifying and diagnosing infection from *Candida* microorganisms such as *C. albicans* through the use of the mp58 mannoprotein, epitopes and peptides as described above and antibodies that recognize such proteins, epitopes and/or peptides. In accordance with the present invention, the antibodies of the invention as set forth above may be used in kits to diagnose *Candida* infections, and such kits may be of the type generally known in the art and commonly used to detect an antigen or microorganism of interest which will bind to the antibodies of the invention. These diagnostic kits will generally include the antibodies of the invention along with suitable means for detecting binding by that antibody such as would be readily understood by one skilled in this art. For example, the means for detecting binding of the antibody may comprise a detectable label that is linked to said antibody. These kits can then be used in diagnostic methods to detect the presence of a *Candida* infection wherein one obtains a sample suspected of being infected by one or more *Candida* microorganisms, such as a sample taken from an individual, for example, from one's blood, saliva, urine, cerebrospinal fluid, genitourinary tract, tissues, bone, muscle, cartilage, or skin, and introduces to the sample one or more of the antibodies as set forth herein. After introduction of the antibodies, it is then determined through conventional means whether there has been binding by the antigens or microorganisms in the sample, such as through suitable labeling, or assays wherein the antibodies are bound to solid supports, and this binding is reflective of the presence of the target antigens or microorganisms in the sample.

Methods for Monitoring Levels of Antibodies or Antigens

In accordance with the present invention, it is also contemplated that another use of the invention will be in monitoring the level of Candidal antigens, or antibodies recognizing said antigens in a human or animal patients suspected of containing said antigens or antibodies. In the preferred process, this may be carried out by first obtaining a biological sample from the human or animal patient, and this would include any suitable sample routinely monitored for infection, such as for example, from one's blood, serum, saliva, tissues, bone, muscle, cartilage, or skin. Next, one would introduce into the sample either (1) when monitoring levels of Candidal antibodies is desired, a determinable level of a Candidal protein or peptide to which Candidal antibodies will bind, such as the proteins and peptides described herein and above, including the mp58 mannoprotein (SEQ ID NO: 2) and its active regions epitopes including SEQ ID NO:4, SEQ ID NO:5, SEQ ID NO:6, SEQ ID NO:7, SEQ ID NO:8, SEQ ID NO:9, SEQ ID NO:10, and SEQ ID NO:11; or (2), when monitoring levels of *Candida* antigens is desired, introducing into said sample a measurable level of a *Candida* antibody in accordance with the present invention which can recognize mp58 or a peptide or epitope as set forth above. The next step in the process is, after allowing sufficient time and conditions so that the antigens and antibodies in the sample can achieve binding, then determining the level of antigen-antibody binding which will be reflective of the amount or level of the Candidal antigens, or antibodies thereto, which are located in the sample. In the desired process, levels may be monitored at regular time periods (e.g., hourly, daily, etc.) so as to track the progression/remission of a Candidal infection during the period of hospitalization or treatment.

Assays for Detecting and Diagnosing Candidal Infections

In accordance with the present invention, the detection of Candidal antigens present in a biological fluid (e.g. blood, serum, plasma, saliva, urine, cerebrospinal fluid, genitourinary tract) or other biological material (e.g., tissues, bone, muscle, cartilage, or skin) can constitute a method for the diagnosis of acute or chronic infections caused by microorganisms of the *Candida* species, including candidiasis. Because the antibodies as set forth above can recognize the epitopes found in several *Candida* yeast, these antibodies can be used in assays to allow the diagnosis of candidal infections and disease conditions. Either monoclonal antibodies or polyclonal antibodies could be used in the assay, and in the case of the monoclonals such as those referred to above, the specific epitopes of the mp58 mannoprotein may be detected as well as the mp58 mannoprotein itself. The detected antigens identified by use of the present assays can be detected by a number of conventional means, including Western immunoblot and other similar tests.

With regard to the assays of the present invention, these assays may use the antibodies of the invention in labeled form, and all well-known methods of labeling antibodies are contemplated, including without limitation enzymatic conjugates, direct labeling with dye, radioisotopes, fluorescence, or particulate labels, such as liposome, latex, polystyrene, and colloid metals or nonmetals. Multiple antibody assay systems, such as antigen capture sandwich assays, are also within the scope of this invention. Further, competitive immunoassays involving labeled protein or assays using the labeled protein to detect serum antibodies are also contemplated forms of the diagnostic assays of the present invention. Beyond diagnostic assays which occur in solution, assays which involve immobilized antibody or protein are also considered within the scope of the invention. (See, for example, Miles et al., Lancet 2:492, 1968; Berry et al., J. Virol. Met. 34:91-100, 1991; Engvall et al., G. Immunochemistry, 8:871, 1971, Tom, Liposomes and Immunology, Elsevier/North Holland, New York, N.Y., 1980; Gribnau et al., J. of Chromatogr. 376:175-89, 1986 and all references cited therein). Examples of the types of labels which can be used in the present invention include, but are not limited to, enzymes, radioisotopes, fluorescent compounds, chemiluminescent compounds, bioluminescent compounds, particulates, and metal chelates. Those of ordinary skill in the art will know of other suitable labels for binding to the monoclonal or polyclonal antibody (or to an antigen) or will be able to ascertain the same by the use of routine experimentation. Furthermore, the binding of these labels to the monoclonal or polyclonal antibody (or antigen) can be accomplished using standard techniques commonly known to those of ordinary skill in the art.

One of the ways in which an assay reagent (generally, a monoclonal antibody, polyclonal antibody or antigen) of the present invention can be detectably labeled is by linking the monoclonal antibody, polyclonal antibody, or antigen to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label the reagents of the present invention include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of the detectably labeled reagent of the present invention can also be detected by labeling the reagent with a radioactive isotope which can then be determined by such means as the use of a gamma counter or a scintillation counter. Isotopes which are particularly useful for the purpose of the present invention are $^3$H, $^{125}$I, $^{32}$P, $^{35}$S, $^{14}$C, $^{51}$Cr, $^{36}$Cl, $^{57}$Co, $^{58}$Co, $^{59}$Fe and $^{75}$Se. It is also possible to detect the binding of the detectably labeled reagent of the present invention by labeling the monoclonal or polyclonal antibody with a fluorescent compound. When the fluorescently labeled reagent is exposed to light of the proper wave length, its presence can then be detected due to the fluorescence of the dye. Among the most commonly used fluorescent labeling compounds are fluorescein isothiocyanate, rhodamine, phycoerythrin, phycocyanin, allophycocyanin, o-phthaldehyde and fluorescamine. The reagents of the present invention also can be detectably labeled by coupling it to a chemiluminescent compound. The presence of the chemiluminescent-tagged reagent is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the reagent of the present invention. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

Another technique which may also result in greater sensitivity when used in conjunction with the present invention consists of coupling the monoclonal or polyclonal antibody of the present invention to low molecular weight haptens. The haptens can then be specifically detected by means of a second reaction. For example, it is common to use such haptens as biotin (reacting with avidin) or dinitrophenol, pyridoxal and fluorescamine (reacting with specific antihapten antibodies) in this manner. Any biological sample containing the detectable yet unknown amount of a Candidal antigen can be used in the assay. Normally, the sample is preferably a liquid, such as, for example, urine, saliva, cerebrospinal fluid, blood, serum and the like, or a solid or semi-solid, such as, for example, tissue, feces and the like.

The diagnostic assay of the present invention includes kit forms of such an assay. This kit would include antibodies to the mp58 mannoprotein and/or its epitopes as described above (raised against whole mp58 mannoproteins or active immunoreactive fragments or analogs thereof) which can be optionally immobilized, as well as any necessary reagents and equipment to prepare the biological sample for and to conduct analysis, e.g. preservatives, reaction media such as nontoxic buffers, microtiter plates, micropipettes, etc. The reagent (Abs and/or antigens) can be lyophilized or cryopreserved. As described above, depending on the assay format, the antibodies can be labeled, or the kit can further comprise labeled mp58 mannoproteins, fragments or analogs thereof containing the relevant epitopes so as to enable the detection of antibodies to mp58 in biological fluids and tissues. By analog is meant a protein or peptide which may differs from its naturally occurring or recombinant counterpart by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end. Accordingly, antibodies in accordance with the invention may also recognize such analogs. The types of immunoassays which can be incorporated in kit form are many. Typical examples of some of the immunoassays which can utilize the antibodies of the invention are radioimmunoassays (RIA) and immunometric, or sandwich, immunoassays.

By "immunometric assay" or "sandwich immunoassay", in meant to include simultaneous sandwich, forward sandwich and reverse sandwich immunoassays. These terms are well understood by those skilled in the art. Those of skill will also appreciate that the monoclonal antibodies, polyclonal antibodies and/or antigens of the present invention will be useful in other variations and forms of immunoassays which are presently known or which may be developed in the future. These are intended to be included within the scope of the present invention. In a forward sandwich immunoassay, a sample is first incubated with a solid phase immunoadsorbent containing monoclonal or polyclonal antibody(ies) against the antigen. Incubation is continued for a period of time sufficient to allow the antigen in the sample to bind to the immobilized antibody in the solid phase. After the first incubation, the solid phase immunoadsorbent is separated from the incubation mixture and washed to remove excess antigen and other interfering substances, such as non-specific binding proteins, which also may be present in the sample. Solid phase immunoadsorbent containing antigen bound to the immobilized antibody is subsequently incubated for a second time with soluble labeled antibody or antibodies. After the second incubation, another wash is performed to remove unbound labeled antibody(ies) from the solid phase immunoadsorbent and removing non-specifically bound labeled antibody(ies). Labeled antibody(ies) bound to the solid phase immunoadsorbent is then detected and the amount of labeled antibody detected serves as a direct measure of the amount of antigen present in the original sample.

Alternatively, labeled antibody which is not associated with the immunoadsorbent complex can also be detected, in which case the measure is in inverse proportion to the amount of antigen present in the sample. Forward sandwich assays are described, for example, in U.S. Pat. Nos. 3,867,517; 4,012,294 and 4,376,110, incorporated herein by reference. In carrying out forward immunometric assays, the process may comprise, in more detail: (a) first forming a mixture of the sample with the solid phase bound antibody(ies) and incubating the mixture for a time and under conditions sufficient to allow antigen in the sample to bind to the solid phase bound antibody(ies), (b) adding to the mixture after said incubation of step (a) the detectably labeled antibody or antibodies and incubating the new resulting mixture for a time and under conditions sufficient to allow the labeled antibody to bind to the antigen-antibody complex on the solid phase immunoadsorbent; (c) separating the solid phase immunoadsorbent from the mixture after the incubation in step (b); and (d) detecting either the labeled antibody or antibodies bound to the antigen-antibody complex on the solid phase immunoadsorbent or detecting the antibody not associated therewith.

In a reverse sandwich assay, the sample is initially incubated with labeled antibody(ies), after which the solid phase immunoadsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110. In carrying out reverse immunometric assays, the process may comprise, in more detail; (a) first forming a mixture of the sample with the soluble detectably labeled antibody for a time and under conditions sufficient to allow antigen in the sample to bind to the labeled antibody; (b) adding to the mixture after the incubation of step (a) the solid phase bound antibodies and incubating the new resulting mixture for a time and under conditions sufficient to allow antigen bound to the labeled antibody to bind to the solid phase antibodies; (c) separating the solid phase immunoadsorbent from the incubating mixture after the incubation in step (b); and (d) detecting either the labeled antibody bound to the solid phase immunoadsorbent or detecting the labeled antibody not associated therewith.

In a simultaneous sandwich assay, the sample, the immunoadsorbent having multiple immobilized antibodies thereon and labeled soluble antibody or antibodies are incubated simultaneously in one incubation step. The simultaneous assay requires only a single incubation and does not include washing steps. The use of a simultaneous assay is by far the preferred one. This type of assay brings about ease of handling, homogeneity, reproducibility, and linearity of the assays and high precision. The sample containing antigen, solid phase immunoadsorbent with immobilized antibodies and labeled soluble antibody or antibodies is incubated under conditions and for a period of time sufficient to allow antigen to bind to the immobilized antibodies and to the soluble antibody(ies). In general, it is desirable to provide incubation conditions sufficient to bind as much antigen as possible, since this maximizes the binding of labeled antibody to the solid phase, thereby increasing the signal. Typical conditions of time and temperature are two hours at 45 degrees C., or twelve hours at 37 degrees C. Antigen typically binds to labeled antibody more rapidly than to immobilized antibody, since the former is in solution whereas the latter is bound to the solid phase support. Because of this, labeled antibody may be employed in a lower concentration than immobilized antibody, and it is also preferable to employ a high specific activity for labeled antibody. For example, labeled antibody might be employed at a concentration of about 1-50 ng per assay, whereas immobilized antibody might have a concentration of 10-500 ng per assay per antibody. The labeled antibody might have a specific activity with, for instance, one radioiodine per molecule, or as high as two or more radioiodines per molecule of antibody.

Of course, the specific concentrations of labeled and immobilized antibodies, the temperature and time of incubation as well as other assay conditions can be varied, depending on various factors including the concentration of antigen in the sample, the nature of the sample and the like. Those skilled in the art will be able to determine operative and optimal assay conditions for each determination by employing routine experimentation.

In carrying out the simultaneous immunometric assay on a sample containing a multivalent antigen, the process may comprise, in more detail: (a) simultaneously forming a mixture comprising the sample, together with the solid phase bound antibody and the soluble labeled antibody or antibodies; (b) incubating the mixture formed in step (a) for a time and under conditions sufficient to allow antigen in the sample to bind to both immobilized and labeled antibodies; (c) separating the solid phase immunoadsorbent from the incubation mixture after the incubation; and (d) detecting either labeled antibody bound to the solid phase immunoadsorbent or detecting labeled antibody not associated therewith. Other such steps as washing, stirring, shaking filtering and the like may of course be added to the assays, as is the custom or necessity for any particular situation.

There are many solid phase immunoadsorbents which have been employed and which can be used in the present invention. Well-known immunoadsorbents include nitrocellulose, glass, polystyrene, polypropylene, dextran, nylon and other materials; tubes, beads, and microtiter plates formed from or coated with such materials, and the like. The immobilized antibodies can be either covalently or physically bound to the solid phase immunoadsorbent, by techniques such as covalent bonding via an amide or ester linkage, or by absorption. Those skilled in the art will know many other suitable solid phase immunoadsorbents and methods for immobilizing antibodies thereon, or will be able to ascertain such, using no more than routine experimentation.

Kits

As indicated above, in accordance with the present invention, the antibodies of the invention as set forth above may be used in kits to diagnose a candidal infection. Such diagnostic kits are well known in the art and will generally be prepared so as to be suitable for determining the presence of fungi, or epitopes or proteins that will bind to the antibodies of the invention. These diagnostic kits will generally include the antibodies of the invention along with suitable means for detecting binding by that antibody such as would be readily understood by one skilled in this art. For example, the means for detecting binding of the antibody may comprise a detectable label that is linked to said antibody. These kits can then be used in diagnostic methods to detect the presence of a candidal infection wherein one obtains a biological sample suspected of having such an infection, such as a sample taken from an individual, for example, from one's blood, saliva, urine, cerebrospinal fluid, genitourinary tract, tissues, bone, muscle, cartilage, or skin, introduces to the sample one or more of the antibodies as set forth herein, and then determines if the antibodies bind to the sample which would indicated the presence of such microorganisms in the sample.

In addition, as set forth above, these kits can also be useful in methods of monitoring the level of Candidal antibodies or antigens in the serum of a human or animal patient. If monitoring the level of Candidal antigen is desired, the kit will include a Candidal antibody in accordance with the present invention as described above along with a means of determining the level of binding to that antibody. When it is desired to measure the level of Candidal antibodies in a sample, the kit will preferably include an isolated Candidal epitopic carbohydrate moietyprotein, or peptide such as described above, e.g., a protein or peptide selected from the group consisting of the mp58 mannoprotein (SEQ ID NO: 2) and its active regions epitopes including SEQ ID NO:4, SEQ ID NO:5, SEQ ID NO:6, SEQ ID NO:7, SEQ ID NO:8, SEQ ID NO:9, SEQ ID NO:10, and SEQ ID NO:11, along with means for detecting binding of those antigens to Candidal antibodies present in the sample.

Treating or Protecting Against Infections

In accordance with the present invention, methods are provided for preventing or treating an infection caused by microorganisms of the species *Candida*, such as *C. albicans*, which comprise administering an effective amount of the antibodies as described above to a human or animal patient in need of such treatment in amounts effective to treat or prevent the infection. Accordingly, in accordance with the invention, administration of an effective amount of the antibodies of the present invention in any of the conventional ways described above (e.g., topical, parenteral, intramuscular, etc.), and will thus provide an extremely useful method of treating or preventing candidal infections in human or animal patients. As indicated above, by effective amount is meant that level of use, such as of an antibody titer, that will be sufficient to either prevent adherence of the yeast or fungi, or to inhibit binding and colonization of candidal organisms to host cells and thus be useful in the treatment or prevention such infections. In addition, these antibodies also exhibit protective effects by a number of other mechanisms, including direct killing of the infectious microorganisms, increased opsonization, inhibition of morphological transition, etc., and thus an effective amount of antibodies will also include that amount by which any of the means to achieve a protective effect is obtained. As would be recognized by one of ordinary skill in this art, the level of antibody titer needed to be effective in treating or preventing infections will vary depending on the nature and condition of the patient, and/or the severity of the pre-existing infection.

Eliciting an Immune Response

In accordance with the present invention, a method is provided for eliciting an immunogenic reaction in a human or animal comprising administering to the human or animal an immunologically effective amount of an isolated mp58 mannoprotein, or an immunogenic fragment, region or epitope as described above so as to elicit an immunogenic response. As indicated above, an "immunogenic amount" of the antigen to be used in accordance with the invention to obtain an immunogenic reaction is intended to mean a nontoxic but sufficient amount of the agent, such that an immunogenic response will be elicited in the host so that the desired prophylactic or therapeutic effect is produced. Accordingly, the exact amount of the isolated protein that is required to elicit such a response will vary from subject to subject, depending on the species, age, and general condition of the subject, the severity of the condition being treated, the particular carrier or adjuvant being used and its mode of administration, and the like. The invention also contemplates methods of generating antibodies which recognize the mp58 mannoprotein and its epitopes as described above, and suitable methods of generating monoclonal and polyclonal antibodies are described in more detail above.

Coating Devices

In accordance with the invention, the antibodies and compositions as described above may also be utilized to treat or protect against outbreaks of yeast and fungal infections on certain medical devices and other implanted materials such as prosthetic devices. Medical devices or polymeric biomaterials that may be advantageously coated with the antibodies and/or compositions described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/ urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or composition as defined above to a surface of the device, preferably an outer surface that would be exposed to a yeast or fungal infection such as those caused by microorganisms of the species *Candida*. The surface of the device need not be entirely covered by the protein, antibody or active fragment.

As indicated above, the antibodies of the present invention, or active portions or fragments thereof, may also be useful for interfering with the physical interaction between a yeast or fungal pathogen responsible for infection and a mammalian host, and may also be useful in interfering with the ability of the yeast or fungus to adhere to extracellular matrix proteins such as fibrinogen. Accordingly, the antibodies of the invention may be useful both in treating patients and in preventing or reducing candidal infections such an candidiasis, or for reducing or eliminating infection and infestation of such organisms in-dwelling medical devices and prosthetics to make them safer for use.

In short, the antibodies of the present invention as described above can be extremely useful in detecting, treating or preventing infections by candidal microorganisms in human and animal patients, or in preventing or reducing infection of medical devices and prosthesis that can be caused by such organisms. In particular, the present invention will be of importance in the treatment or prevention of such infections in highly susceptible groups such as premature newborns, AIDS and debilitated cancer patients, and are particularly frequent and severe after bone marrow transplantation.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification and Characterization of Cell Wall Proteins and Mannoproteins from *Candida albicans*

Introduction:

The 58-kilodalton mannoprotein (mp58) on the surface of *Candida albicans* is highly immunogenic, is expressed by all *C. albicans* isolates tested, and elicits strong antibody responses during candidiasis. It belongs to a family of immunodominant fungal antigens with homologs also in different species of *Aspergillus*. The amino acid sequence of the protein portion of mp58 as deduced from the DNA sequence of its encoding gene (FBP1/PRA1) was used to synthesize a complete set of overlapping dodecapeptides (overlap, 7; offset, 5) covalently attached to the surface of derivatized polyethylene pins. The pin-coupled peptides were used in a modified enzyme-linked immunosorbent assay (ELISA) to identify continuous epitopes recognized by a number of antiserum preparations containing anti-mp58 antibodies. This comprehensive epitope-scanning study revealed the presence of multiple immunoreactive continuous B-cell epitopes within the protein sequence. Regions of increased reactivity included both the amino and carboxy termini of the mature protein (encompassing amino acid residues 16 to 50 and 286 to 299, respectively) and four internal regions spanning amino acids at positions 66 to 92, 121 to 142, 148 to 192, and 211 to 232. Further delineation of epitopic regions and identification of the boundaries of the antigenic sites was performed upon ELISA testing with a second Pepset consisting of completely overlapping 8-mer peptides spanning these reactive regions in the protein moiety of mp58. The highly reactive epitopic region at the C terminus of the protein was further evaluated using both window net and replacement net analyses. A synthetic peptide corresponding to the last 10 amino acid residues at the C terminus of the protein was immunogenic when injected into mice after being coupled to a carrier protein. Moreover, antibodies in the resulting sera specifically recognized the homologous mp58 in ELISAs and immunoblot assays. Delineation of the antibody responses to mp58 could provide the basis for the development of novel immunity-based prophylactic, therapeutic, and diagnostic techniques for the management of candidiasis.

Background and Significance:

*Candida albicans* is a dimorphic fungus that is both a commensal and opportunistic pathogen of man. Depending on the underlying host defect, *Candida* is able to cause a variety of infections that range from mucosal to life-threatening disseminated candidiasis, having the ability to infect virtually every organ in the host (1, 2). Predisposing factors for candidiasis include immunosuppressive therapy, massive antibiotic therapy, cytotoxic therapy, intravenous catheters and indwelling devices, very low birth weight, AIDS, diabetes, transplantation medicine, drug dependency, etc. (1). The lack of an early and accurate diagnostic procedure, the high toxicity exhibited by the most common and effective treatments, and the emergence of resistant strains due to empirical prophylactic treatment are responsible for the high morbidity and mortality rates associated with disseminated infections (3). Because of these reasons, there is an increasing interest in the development of preventive strategies and in the search for new or alternative therapies to enhance or complement a multicomponent approach to the management of candidiasis. However, despite the efforts of numerous groups of investigators, our present understanding of the pathogenicity mechanisms of this microorganism, as well as our knowledge of factors determining host susceptibility, are still exploratory areas. A proposed list of putative virulence factors of *C. albicans* would include morphological transition, antigenic variability, phenotypic switching, adhesion to host structures, cell surface hydrophobicity, molecular mimicry, and production of extracellular enzymes (4). As the outer most part of the cell, the cell wall is the structure in which most of these activities reside. The cell wall of *C. albicans* is a complex multilayered structure in which glucan and chitin form a rigid microfibrillar network, and proteins and glyco(manno)proteins are embedded in this skeleton as well as being present in the outer surface (5). Today, the cell wall is envisaged as a highly dynamic organelle with the capacity of differentially expressing variable constituents useful for adaptation to a commensal or pathogenic life style. Proteins and mannoproteins are thought to play important roles from both a structural and a physiological point of view, and may be involved in processes such as morphogenesis (6, 7), cell surface hydrophobicity (8-11), adherence (12-15), and antigen presentation and immunomodulation (5, 16).

As mentioned earlier, pathogenicity is also dependent on host-related factors. More concretely, the immunological status of the host seem to be of special relevance for susceptibility to fungal infections. In the case of *C. albicans* and other pathogenic fungi, the importance of cellular defense mechanisms for protection is supported by the fact that most invasive manifestations are detected in patients with deficiencies in cellular immunity (17). Cell-mediated immunity (T cells) and nonspecific cellular immunity (macrophages, neutrophils and NK cells) are generally believed to play important roles in protection against candidiasis (17). However, the role of humoral immunity in candidiasis and other fungal infections remains a controversial issue, with contradictory reports that either support or deny the importance of antibody immunity (18). Some of the contradictory evidences for and against the importance of antibody immunity may be explained by the complex nature of the humoral response, with the presence in immune sera of protective, non-protective, and infection-enhancing antibody responses (18). There are a number of mechanisms by which antibody to *C. albicans* can contribute to host defense. Our group has previously described that Fab fragments of a MAb to a hyphal antigen inhibit the yeast-to-mycelium transition which is associated with increased adherence and invasion (6) and we have also demonstrated that antibodies against cell wall components prevent adhesion to host tissues (19). Antibodies can also display direct candidacidal activity (20), opsonic antibodies can stimulate phagocytosis (21), and they can bind to immunomodulating polysaccharides (22). In the recent years there has been a body of convincing evidence that some antibodies can display an immunoprotective mechanism, favoring the host during the course of infection, thus suggesting the viability of a vaccine approach to the prevention of candidiasis. Recent reports clearly demonstrate that some antibodies can mediate protection in mucosal (vaginal) candidiasis (20, 23-25). More importantly, in the case of disseminated infection, patient recovery was found to correlate with the presence in the serum of antibodies against the *C. albicans* HSP90 (26-29). More recently, Han and Cutler demonstrated that antibodies against mannan adhesins can aid the host to resist disseminated candidiasis (30). It is important here to stress the fact that in both cases the molecules eliciting antibody-protective response (HSP90 and the mannan adhesin) are cell wall components (the 47 kDa cell wall moiety is a breakdown product of HSP90, 31), and this observation could be related to the location and functions of cell wall components discussed above.

Our work has focused on the identification and characterization of cell wall proteins and mannoproteins of *C. albicans*, with a special interest in those surface components implicated in adhesion to host cells and tissues. In *C. albicans*, as in several other pathogenic microorganisms, adhesion of the fungus to host cells and tissues is considered to be the initial step leading to establishment of infection, and then hematogenous dissemination can lead to metastatic infection throughout the body (12, 13). These adhesion processes are mediated by complementary molecules in both the surface of the fungus and the host. In this context, several categories of receptor-like molecules (also designated with the term adhesins) have been identified on the surface of *C. albicans*, including molecules with integrin- and lectin-like activities, along with species in which the sugar moieties (most commonly known as mannan) seem to play an essential role in the interactions (12). Adhesins described so far include a molecule that presented cross-reactivity towards an antisera raised against the integrin $\beta_1$ subunit (32), receptors for complement fragments iC3b and C3d (33-37), different serum proteins (38-40) and a number of extracellular matrix (ECM) components such as laminin (41, 42), fibronectin (43-46), collagens (43, 45), entactin (19) and vitronectin (47); moieties that mediate binding to plastic (48) and responsible for cell surface hydrophobicity (10, 11); a unique adhesion system involving mannan moieties by which the fungus binds to macrophages in spleen and lymph-node (49-53); fimbrial adhesins (54, 55); and an extracellular adhesin which mediates attachment to epithelial cells (56, 57). This repertoire of adhesins displayed by *Candida* is probably a reflection of the range of sites that it can invade in the host, and contribution of the different receptor-like molecules to adhesion may be different depending on the type of cell or tissue in consideration, whether it is an epithelial cell, normal endothelium or exposed extracellular matrix (12, 14). We have identified, characterized, and cloned a 58 kDa fibrinogen-binding mannoprotein (mp58) on the surface of *C. albicans*, and raised a polyclonal antibody (PAb anti-mp58) against the purified component (39). The mp58 appears to be a major component in β-mercaptoethanol (β-ME) cell wall extracts of both morphological phases of the fungus. It is both N- and O-glycosylated. Confocal microscopy studies revealed that the mp58 is heterogeneously distributed along the surface of the fungus (58). It is different from other surface adhesins such as laminin receptors (41, 42), entactin receptors (19), and receptors binding complement factors (59), and it is highly hydrophobic (11, 60). The mp58 is expressed in all *C. albicans* strains tested, including collection strains and fresh clinical isolates. Moreover, it is expressed in fungal cells infecting tissues (39). Sera from patients suffering from disseminated candidiasis but not from those suffering from superficial forms of the disease and control (normal) individuals contain antibodies against mp58. These observations seem to suggest an active role for mp58 during the interaction between *C. albicans* and the host.

Identification and Characterization of a 58 kDa Cell Surface Fibrinogen-binding mannoprotein of *C. albicans*.

A number of studies have shown a high degree of complexity associated with the protein composition of the cell wall. In general, polyacrylamide gel electrophoresis (PAGE) and Western-blot techniques have been used to study and analyze the proteins and mannoproteins of the candidal cell wall (61-65). We have described a combination of chemical (β-ME) and enzymatic (Zymolyase) solubilization techniques leading to the release of genuine cell wall components from intact cells of C. albicans (61, 62). Treatment of both yeast cells and germ tubes of C. albicans with β-ME led to solubilization of a complex array of proteins and mannoproteins. Ligand affinity blotting with a combination of fibrinogen and anti-fibrinogen antibody allowed detection of a 58 kDa component (mp58) in extracts from both fungal morphologies which specifically interacts with human fibrinogen (39). The mp58 is a mannoprotein as indicated by its reactivity against Concanavalin A (ConA). Also, it is highly hydrophobic as determined for its ability to bind polystyrene-latex microbeads (11, 60). Strong fluorescence was observed when C. albicans germ tubes were incubated in the presence of fibrinogen in an indirect immunofluorescence experiment. Most of the mother blastospores from which the germ tubes originate, as well as non-germinated yeast cells exhibited a faint fluorescence; however a relative low percentage of non-germinating blastospores showed intense fluorescence. The mp58 was purified and the purified preparation was injected to rabbits to generate polyclonal antisera against this component (PAb anti-mp58). When this polyclonal antiserum was used in immunoblot and IIF techniques, the recognition patterns were basically identical to those detected for fibrinogen binding. See FIG. 1.

The heterogeneous distribution of mp58 along the surface of C. albicans cells was further confirmed by confocal microscopy using both binding of fibrinogen and PAb anti-mp58 as probes in an IIF assay (58). Clustering of receptors could increase the security of the interactions between the microbe and the host. Human tissue specimens obtained at the times of autopsy (necropsy) from patients with confirmed systemic candidiasis and biopsy samples from individuals with superficial cutaneous and urethral candidiasis were processed for immunohistochemical staining using the PAb anti-mp58 (39). These experiments revealed that the mp58 is expressed in high levels on the surface of C. albicans cells infecting human tissues, and thus suggest a role for mp58 during infection. The glyco(manno)protein nature of mp58 was further investigated. Treatment with Endo H, which cleaves the N-linked carbohydrate moieties resulted in the conversion of the native mp58 to a 47 kDa species. This band, which was still recognized by PAb anti-mp58 and able to bind ConA, retained the ability to bind fibrinogen. β-elimination, which removes O-linked oligosaccharides, did not significantly modify the electrophoretic mobility of mp58, as its molecular mass was reduced approximately by 1.5 kDa. Interestingly, the O-deglycosylated species exhibited unaltered reactivity with ConA and PAb anti-mp58, but was unable to interact with fibrinogen, suggesting a role for O-linked sugar residues in binding of fibrinogen.

Several laboratories reported similar sizes for proteins of C. albicans binding different host ligands, such as complement factors, laminin, and fibrinogen, but the relationship is unclear. Also, the existence of multiple biological activities for these candidal receptors has been postulated (66). These observations prompted us to investigate the possible relationship between the mp58 with other candidal receptors for human proteins. Experiments described in the next paragraphs clearly demonstrate that mp58 is different from other C. albicans molecules displaying receptor-like activities.

Comparative Study of the mp58 and the Candidal Receptor for Complement Fragment C3d.

Some of the similarities between these two receptor-like molecules as reported in previous studies include: i) both molecules are glyco(mannoproteins), ii) neither of them present a complete morphologic specificity, iii) both have a similar apparent molecular weight (around 60 kDa), iv) are found in cell wall materials extracted with similar techniques, v) are expressed in vivo in infected tissues, and vi) both are found in the material secreted to the liquid medium (34, 37, 39, 60, 67, 68). However, some differences between both molecules also exist; perhaps the most important is that in the case of the C3d receptor, the protein moiety has been the structure implicated in ligand-binding (13), whereas in the case of the 58 kDa mannoprotein, fibrinogen binding appears to be mediated by the sugar moieties of the molecule (39), although it can also be possible that binding of different ligands occurs via different domains of the same molecule. Also, using microscopy techniques, recognition patterns have been described to be different for both antisera, although these differences may be due to the different growing conditions employed in these studies (39, 69).

We have used antibodies raised against the C. albicans C3d-receptor (CR2, PAb anti-CR2) and mp58 (PAb anti-mp58), as well as ligand interactions to study the relationship between these two molecules and their possible homology (59). In an indirect immunofluorescence assay, higher recognition in the mother blastospores occurred when we used PAb anti-CR2; whereas we observed higher intensity levels of fluorescence in the hyphal elongations when we used as probes PAb anti-mp58 or binding of soluble fibrinogen. No competition or change in the fluorescence pattern was observed in dual labeling experiments using the PAb anti-CR2 receptor and either fibrinogen or PAb anti-mp58. In immunoblots, PAb anti-CR2 recognized three different discrete bands in the β-ME extracts from the cell wall, whereas a different single broader band was detected in the case of the PAb anti-mp58. However, when non-denaturing conditions were used to separate the materials present in the cell-wall extracts no reactivity could be detected with PAb anti-mp58 in Western-blots. When PAb anti-CR2 was used as a probe, a single band migrating in the area corresponding to approximately 40 kDa was detected. These observations suggest higher molecular mass for these molecules in their native state, thus indicating that these molecules are interacting either with themselves or with other cell wall moieties as part of the cell wall structure. In exploring their relationship and possible interactions between these receptor-like molecules and other cell wall moieties, and more concretely the molecule carrying the epitope recognized by MAb DC3H10 (70), a complex interaction between these molecules in the overall cell wall organization was suggested (71).

Comparative Study of the mp58 and the Candidal Laminin Receptors.

Laminin is a major component of basement membranes (a specialized from of extracellular matrix, ECM) where it interacts with other components such as type IV collagen and entactin. It is a large multidomain glycoprotein which seems to play a critical role not only during normal cell adhesion, but also during tissue invasion and metastasis by tumor cells and microorganism. Laminin receptors of an approximate molecular mass of 68-70 kDa and specific for mycelial cells of C. albicans have been described (41). However, under our experimental conditions, and using affinity blotting experiments (see above), the mp58 moiety specifically interacted with fibrinogen, and it was not able to bind laminin or fibronectin. Moreover, in the case of laminin, we detected two polypeptides of 37 and 67 kDa exclusively present in the p-ME extracts from C. albicans blastospores that had the ability to interact with laminin using the same ligand affinity blotting technique (42). The 37 kDa moiety (p37) showed antigenic homology with the human high-affinity laminin receptor, and it was heterogeneously distributed on the surface of *C. albicans* blastospores as shown by IIF, with similar fluorescence patterns to the ones detected for mp58. However, in a dual fluorescence label experiment, and using fibrinogen binding as a probe for mp58, and binding of a polyclonal antibody generated against the purified p37 (PAb anti-p37) as a probe for p37 we observed that the areas of concentration of each receptor were different, revealing that these components were not co-localized as a potential receptor complex.

Characterization of Binding of Entactin to *C. albicans*.

Entactin (also known as nidogen) is a sulfated glycoprotein and a component of the basement membrane, where it forms a tight stoichiometric complex with laminin and interacts with type IV collagen. We investigated the interaction between *C. albicans* and this recently characterized ECM component (19). Both morphologies of the fungus, blastospores and blastospores-bearing germ-tubes, had the ability to bind recombinant entactin as detected by an indirect immunofluorescence assay. Materials present in the p-ME cell-wall extracts from both *C. albicans* growing forms were capable of binding to immobilized recombinant entactin in a dose-dependent manner, and binding to entactin was approximately twice the one observed for laminin. Interaction between entactin and *C. albicans* was partially inhibited by an Arg-Gly-Asp-Ser (RGDS) (SEQ ID NO: 12) peptide. This may be an indication that the entactin receptors of *C. albicans* belong to the integrin family of receptors, as it has been reported for entactin receptors of mammalian cells (72). A polyclonal anti-entactin antisera, as well as a pooled antisera preparation raised against components present in different *C. albicans* cell wall extracts completely or almost completely abolished binding. The existence of morphology-specific receptor-like molecules which bind to different domains of the entactin molecule was ruled out in a competition binding assay. The entactin-binding material(s) in the cell wall showed a certain degree of promiscuity, since they also displayed some ability to bind laminin and fibronectin. Moieties with molecular masses of approximately 25, 44, and 65 kDa present in the β-ME cell wall extracts from both blastospores and germ-tubes were detected in a ligand-affinity-blotting experiment as having the ability to bind entactin. These moieties were clearly different to the mp58 also present in the same extracts. To our knowledge, this is the first report in the literature suggesting a role for entactin in interaction with non host moieties, and more concretely in binding of a pathogenic microorganism, observation that may have important implications in pathogenesis.

Expression of the Fibrinogen Binding Mannoprotein (mp58) in Clinical Strains of *C. albicans*.

Figure 2:
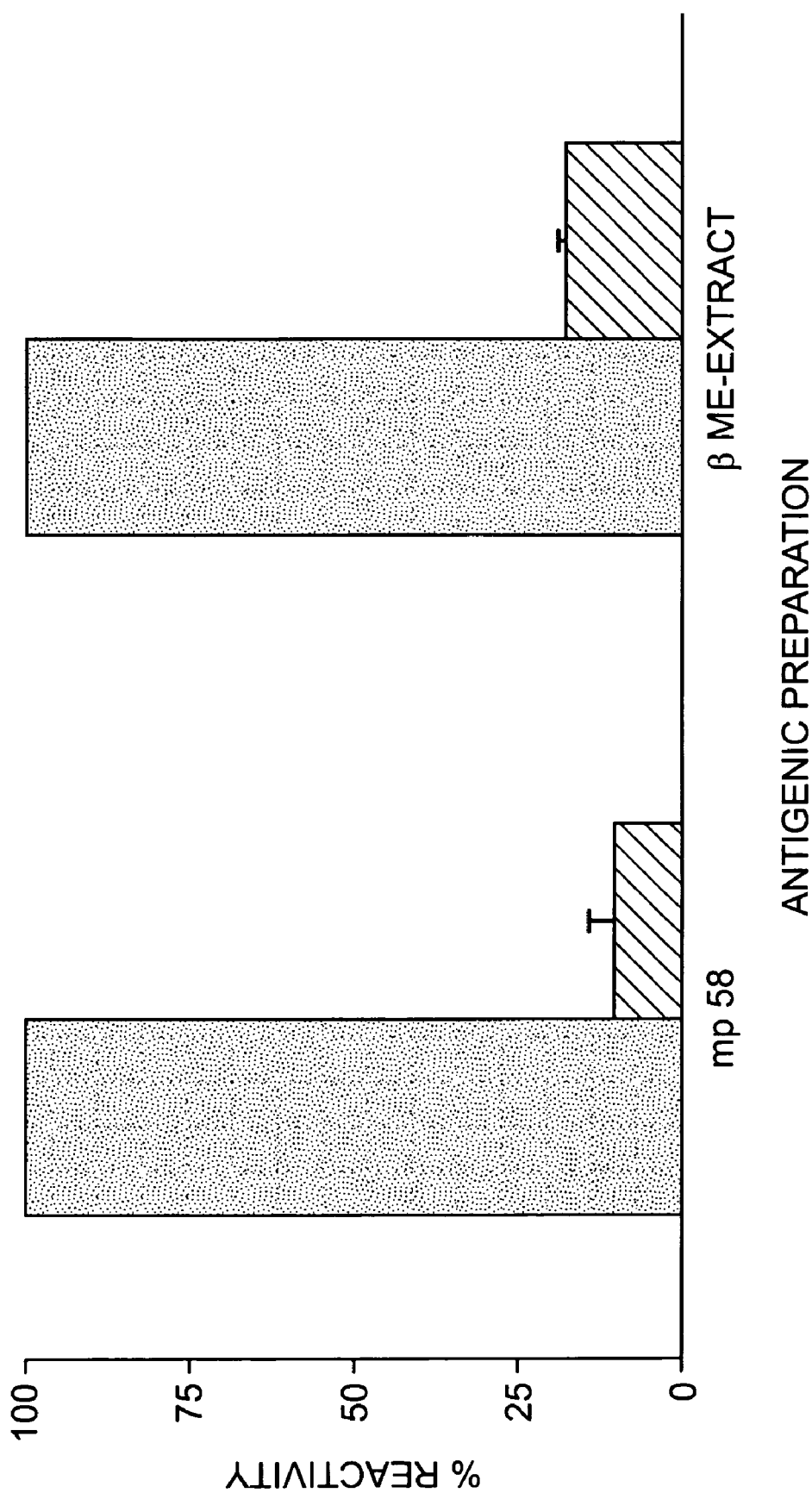

We have investigated the presence of the mp58 in the cell wall of different *C. albicans* clinical isolates propagated under conditions that favor growth as blastoconidia or blastoconidia bearing germ-tubes. Analysis of the overall protein composition associated with the β-ME cell wall extracts from the different strains showed a high degree of complexity and a certain degree of variability, with both qualitative and quantitative differences being detected. However, using a combination of techniques, a moiety with an electrophoretic mobility of approximately 58 kDa, and which appears to be a major component in the extracts, was detected for all strains tested. Immunoblot analysis with a monovalent polyclonal antibody generated against the mp58 revealed differences in recognition patterns depending on strain and culture conditions. The majority of strains appear to have a functional mp58, as detected by the ability to bind fibrinogen in a ligand-affinity experiment. These results suggest that the mp58 is consistently present in all strains tested, and could be a potential antigenic marker for disseminated candidiasis. See FIG. 2.

Epitope Mapping with Antibodies in Sera from Candidiasis Patients.

Figures 3A, 3B:
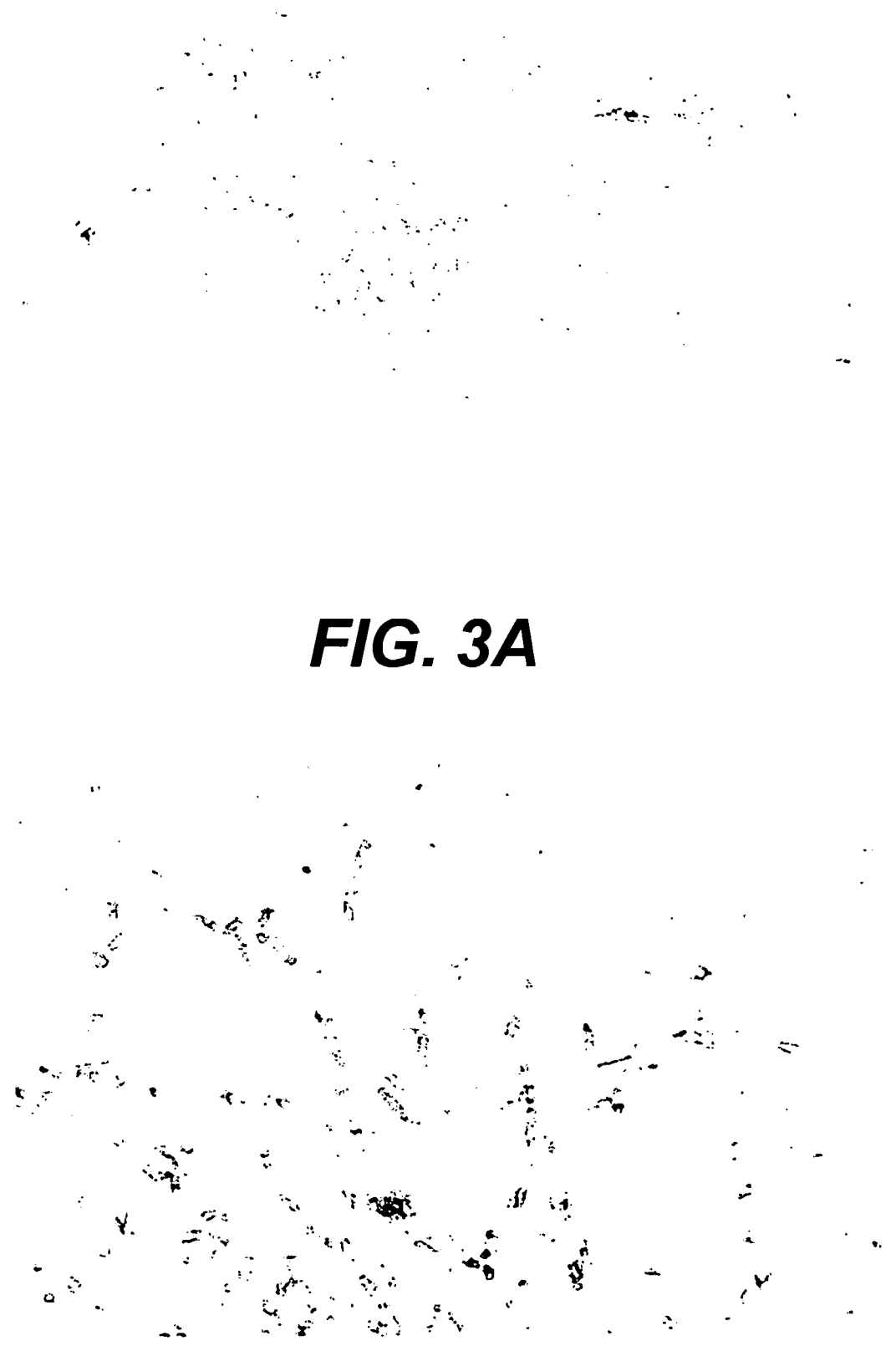

Through our previous studies, the amino acid sequence of the protein part of mp58 is known. The 299 amino acid residues of mp58 were synthesized and bound to pins as complete sets of overlapping dodecapeptides (12 mer) offset along the sequence by five residues. In doing so, all sequences of eight residues from the protein are represented in at least one peptide. These overlapping peptides covered the entire sequence of the protein, which includes a 15 amino acid signal peptide and a mature protein containing 284 amino acids. The final Pepset consisted of a total of 59 peptides, plus 2 control peptides. The resulting pin-set is compatible with the standard 8×12 microplate format and can be scanned in search for B-cell epitopes using a modified ELISA procedure. In a first series of experiments, the pin-coupled peptides were used in a modified enzyme-linked immunosorbent assay to identify continuous epitopes recognized by IgG antibodies present in a serum samples from patients with systemic candidiasis. The IgG reactive domains identified were similar to the ones identified using sera from animals immunized with *C. albicans* mp58 (Viudes et al, I & I, 2001). Two dodecapeptides in the protein sequence exhibited increased reactivity with serum from patients with disseminated candidiasis as compared to reactivities using serum samples from control (non infected) individuals (see FIG. 3).

A synthetic peptide corresponding to the last ten amino acid residues at the C-terminus of the protein ($^{290}$HTHAD-GEVHC$^{298}$) (SEQ ID NO:10) was immunogenic when injected to two mice after coupling to a carrier protein. Moreover, the resulting sera specifically recognized the homologous mp58 in ELISA and immunoblot assays. Initial experiments were directed to optimize an synthetic peptide-based antibody-capture assay to examine presence of antibodies against this mimetic sequence in human serum samples. The following parameters of the antibody-capture ELISA were assessed: i) use of free peptides as compared to the use of KLH-conjugated peptides as materials for coating the wells, iii) use of different quantities of peptide for coating the wells of microtiter plates, iii) use of different types of ELISA plates for optimal adsorption of synthetic peptides, including different types of plastics and chemistry-modified plates, iv) use of different coating buffers, v) use of different blocking reagents including protein and detergents and vi) use of different dilutions of sera. In its final format the KLH-conjugated peptide was used to coat Immulon 2 plates in a carbonate Buffer (pH 9.6) at a concentration of 1 µg/well, after overnight incubation at 4° C. and washes with PBS the different serum samples from patients with candidiasis (1:1,000 dilution in PBS with 0.05% TWEEN 20 [PBST] and 1% BSA) were added to the wells and incubated for 1 h at 37° C. Then the plates were washed with PBST and incubated with peroxidase-conjugated goat-anti human IgG (1:2,000 dilution) for 1 h at 37° C. After washings, the plates were developed (OPD in citrate buffer) and read at 490 nm in a microtiter plate reader. Once the assay was optimized, a larger number of serum samples from patients with disseminated candidiasis (n=13) and control individuals (n=22) were tested. These experiments confirmed the increased levels of antibodies against this peptide in serum samples from patients with disseminated candidiasis as compared to control individuals (FIG. 4, panels A and B).

Moreover, levels of anti-peptide antibodies were significantly higher in surviving patients compared to those with fatal outcomes (FIG. 4, Panel C) thus indicating that this peptide may represent a protective epitope during candidiasis. (importantly levels of reactivity against C. albicans cytosolic and 2ME extracts of antibodies in sera from good and fatal outcome were similar, so higher levels of reactivity against the C-terminal peptide are not due to overall higher antibody levels in survivor vs. those who succumbed to the infection)

Figure 5:

The serum samples from patients with candidiasis were tested by ELISA to assess the distribution of IgG subclasses directed against the C-terminal peptide. Although the nature of these experiments did not allow an accurate quantification of the different immunoglobulins subclasses, results indicated that immunoglobulin G (IgG) antibody subclasses were IgG2>IgG1>IgG3>IgG4. Results indicate a mixed Th1/Th2 response, with overall predominance of Th1, which has been correlated with protection against candidiasis (Romani, L. 1999. Immunity to *Candida albicans*: Th1, Th2 cells and beyond. Curr. Opin. Microbiol. 2:363-7). See FIG. 5.

Generation of monoclonal antibody 3H3. For purification of mp58, components in the βME were separated by preparative sodium dodecyl sulfate-polyacrylamide gel electrophoresis (SDS-PAGE) under denaturing conditions as described by Laemmli. The transverse sections of the gels corresponding to mp58 (as identified by Coomassie staining) were excised, crushed and the polypeptide moieties electroeluted. Pure mp58 was mixed with adjuvant, and injected to BALB/c mice. Immunization protocols consisted of a first injection (using complete Freund's adjuvant), two subsequent booster injections (with incomplete Freund's adjuvant) at three-week intervals, and one final booster injection without adjuvant three days prior to fusion (all injections were subcutaneous). For hybridoma production, mice were sacrificed and their spleen removed aseptically. Antibody secreting cells isolated and mixed with myeloma cells (NS1) using drop-wise addition of polyethylene glycol. After the fusion, cells were diluted in selective medium (vitamin-supplemented DMEM/HAT) and plated at low densities in multiwell tissue culture dishes. Tissue supernatants from the resulting fusion were screened by both ELISA (using the total 2-ME extract to coat the wells of a microtiter plate) and immunoblot techniques. Cells from these positive wells were grown and single cell cloned by limiting dilution, and supernatants subjected to one more round of screening by both ELISA and immunoblot. Positive clones were identified, and monoclonal antibodies collected as hybridoma supernatants, including 3H3, which is an IgG1.

Determination of the epitope recognized by Mab 3H3 was performed by means of the Multipin Peptide Technology (see above) demonstrated that this Mab recognized the C-terminal epitope previously identified as highly reactive by using polyclonal antisera preparations. (Viudes et al, I & I 2001). Further delineation of the epitope recognized by Mab 3H3 was performed using window-net and replacement-net approaches. The window-net analysis identified the nonapeptide $^{290}$HTHADGEVH$^{298}$ (SEQ ID NO: 11) as the minimal region that retained most of the antibody-binding activity for Mab 3H3. The replacement net analysis revealed the important role of the histidines (residues 290, 292 and 298) in the recognition by antibodies, since single substitutions of each of these histidine residues resulted in abrupt decrease in levels of reactivity.

Polyclonal Antibody Response to Peptide HTHADGEVHC (SEQ ID NO: 10).

A synthetic peptide corresponding to the C-terminal decapeptide of mp58 (HTHADGEVHC, SEQ ID NO: 10, the identified nonapeptidic epitope plus the native terminal cysteine) was immunogenic when conjugated to a carrier protein (KLH) and injected into mice. The resulting sera were characterized by a variety of immunological procedures. Hyperimmune sera recognized the free peptide bound to the wells of microtiter plates in a dose-dependent and saturable manner. Both antisera generated contained high titers of anti-peptide antibodies as determined by an endpoint ELISA. Free soluble peptide was an effective competitor of antibody binding to bound peptide and mp58, indicating the specificity of the reaction. The anti-peptide antisera recognized the homologous C. albicans mp58, and no cross-reactivity with other antigens present in cell wall extracts was detected. This result suggested that immunization with a single peptide motif led to a highly specific antibody response and that this decapeptide lacks significant sequence homology with other candidal antigens.

Passive Immunization with Monoclonal Antibody (mAb) 3H3 Protects Against Hematogenously Disseminated Candidiasis.

The protective effects of Mab 3H3 were assessed in a murine model of hematogenously disseminated candidiasis. Briefly, Mab 3H3 ascitis at two different concentrations (high dose [approx 1.8 mg of IgG] and low dose [approx 0.3 mg of IgG], a control group received saline injections) was passively administered to groups of mice via IP about 2 hours prior to infection with a lethal intravenous challenge with 1×10$^6$ cells of C. albicans Confirmation of the number and viability of cells present in the infecting inocula was performed by plate count. Examination of protective effects was performed by monitoring survival daily after infection. Survival data and differences between groups were analyzed using the Kaplan-Meir test. Results indicated that the high dose of 3H3 significantly increased survival compared to the control group (p=0.015), with 4/6 treated animals surviving for longer than 15 days. (compared to 0/6 controls).

The following references cited in conjunction with Example 1 are incorporated in their entirety as if set forth in full herein:

1. Bodey, G. P. 1993. Candidiasis; Pathogenesis, diagnosis and treatment. Raven Press, New York.
2. Odds, F. C. 1988. Candida and candidosis. A review and bibliography. Bailliere Tindall, London.
3. Meunier, F. 1989. Candidiasis. Eur. J. Clin. Microbiol. Infect. Dis. 8:438-447.
4. Cutler, J E. 1991. Putative virulence factors for *Candida albicans*. Annu. Rev. Microbiol. 45:187-2184.
5. Cassone, A. 1989. Cell wall of *Candida albicans*, its functions, and its impact on the host. Curr. Top. Med. Mycol. 3:249-314.
6. Casanova, M., J. P. Martinez, and W. L. Chaffin. 1990. Fab fragments from a monoclonal antibody against a germ tube specific mannoprotein block yeast-to-mycelium transition in *Candida albicans*. Infect. Immun. 58:3810-3812.
7. Martinez, J. P., J. L. López-Ribot, M. L. Gil, R. Sentandreu, and J. Ruíz-Herrera. 1990. Inhibition of the dimorphic transition of *Candida albicans* by the ornithine decarboxylase inhibitor 1,4-diamino-butanone: alterations in the glycoprotein composition of the cell wall. J. Gen. Microbiol. 136:1937-1943.
8. Hazen, B. W., and K. C. Hazen. 1988. Dynamic expression of cell surface hydrophobicity during initial yeast cell growth and before germ tube formation of *Candida albicans*. Infect. Immun. 56:2521-2525.
9. Hazen, K. C., and B. W. Hazen. 1992. Hydrophobic surface protein masking by the opportunistic fungal pathogen *Candida albicans*. Infect. 1 mm. 60:1499-1508.
10. Hazen, K. C., J. G. Lay, B. W. Hazen, R. C. Fu, and S. Murthy. 1990. Partial biochemical characterization of cell surface hydrophobicity and hydrophilicity of *Candida albicans*. Infect. Immun. 58:3469-3476.
11. López-Ribot, J. L., M. Casanova, J. P. Martinez, and R. Sentandreu. 1991. Characterization of cell wall proteins of yeast and hydrophobic mycelial cells of *Candida albicans*. Infect. Immun. 59:2324-2332.
12. Calderone, R. A. 1993. Recognition between *Candida albicans* and host cells. Trends in Microbiol. 1:55-58.
13. Calderone, R. A., and P. C. Braun. 1991. Adherence and receptor relationships in *Candida albicans*. Microbiol. Rev. 55:1-20.
14. Hostetter, M. K. 1994. Adhesins and ligands involved in the interaction of *Candida* spp. with epithelial and endothelial surfaces. Clin. Microb. Rv. 17:29-42.
15. Pendrak, M. L. and Klotz, S. A. 1995. Adherence of *Candida albicans* to host cells. FEMS Microbiol. Lett. 129:103-114.
16. Ausiello, C. M., F. Urbani, S. Gessani, G. Spagnoli, M. J. Gomez, and A. Cassone. 1993. Cytokine gene expression in human peripheral blood mononuclear cells stimulated by mannoprotein constituents from *Candida albicans*. Infect. Immun. 61:4105-4111.
17. Levitz, S. M. 1992. Overview of host defenses in fungal infections. Clin. Infect. Dis. 14 (Suppl.):S37-S42. 18. Casadevall, A. 1995. Antibody immunity and invasive fungal infections. Infect. Immun. 63:4211-4218.
19. Polonelli, L., F. de Bernardis, S. Conti, M. Boccanera, M. Gerloni, G. Morace, W. Magliani, C. Chezzi, and A. Cassone. 1994. Idiotypic intravaginal vaccination to protect against candidal vaginitis by secretory, yeast killer toxin-like antiidiotypic antibodies. J. Immunol. 152:3175-3182.
20. Han, Y., and J. E. Cutler. 1995. Antibody response that protects against disseminated candidiasis. Infect. Immun. 63:2714-2719.
21. López-Ribot, J. L., and W. L. Chaffin. 1994. Binding of the extracellular matrix component entactin to *Candida albicans*. Infect. Immun. 62:4564-4571.
22. Chilgren, R. A., R. Hong, and P. Quie. 1968. Human serum interactions with *Candida albicans*. J. Immunol. 101:128-132.
23. Fischer, A et al. 1978. Specific inhibition of in vitro Candida-induced lymphocyte proliferation by polysaccharide antigens present in the serum from patients with chronic mucocutaneous candidiasis. J. Clin. Invest. 62:1005-1013.
24. Cassone, A., M. Boccanera, D. Adriani, G. Santoni, and F. de Bernardis. 1995. Rats clearing a vaginal infection by *Candida albicans* acquire specific, antibody-mediated resistance to vaginal reinfection. Infect. Imm. 63:2619-2624.
25. Fidel, P. L., M. E. Lynch, and J. D. Sobel. 1995. Circulating CD4 and CD8 T cells have little impact on host defense against experimental vaginal candidiasis. Infect. Immun. 63:2403-2408.
26. Fidel, P. L., J. L. Cutright, and J. D. Sobel. 1995. Effects of systemic cell-mediated immunity on vaginal candidiasis in mice resistant and susceptible to *Candida albicans* infections. Infect. Immun. 63:4191-4194.
27. Mathews, R. C., and J. P. Burnie. 1989. Cloning of a DNA sequence encoding a major fragment of the 47 kilodalton stress protein homologue of *Candida albicans*. FEMS Microbiol. Lett. 60:25-30.
28. Mathews, R. C., J. P. Burnie, D. Howat, T. Rowland, and F. Walton. 1991. Autoantibody to HSP 90 can mediate protection against systemic candidosis. Immunology. 74:20-24.
29. Mathews, R. C., J. P. Burnie, D. Smith, I. Clark, J. Midgley, M. Conolly, and B. Gazzard. 1988. *Candida* and AIDS: evidence for protective antibody. Lancet 11:263-266.
30. Mathews, R. C., J. P. Burnie, and S. Tabaqchali. 1987. Isolation of immunodominant antigens from sera of patients with systemic candidiasis and characterization of serological response to *Candida albicans*. J. Clin. Microbiol. 25: 230-237.
31. Mathews, R. C., C. Wells, and J. P. Burnie. 1988. Characterisation and cellular localisation of the immunodominant 47-kDa antigen of *Candida albicans*. J. Med. Microbiol. 27:227-232.
32. Marcantonio, E. E., and R. O. Hynes. 1988. Antibodies to the conserved cytoplasmic domain of the integrin $\beta_1$ subunit react with proteins in vertebrates, invertebrates, and fungi. J. Cell. Biol. 106:1765-1772.
33. Alaei, S., C. Larcher, C. Ebenbichler, W. M. Prodinger, J. Janatova, and M. P. Dierich. 1993. Isolation and biochemical characterization of the iC3b receptor of *Candida albicans*. Infect. Immun. 61:1395-1399.
34. Calderone, R. A., L. Linehan, E. Wadsworth, and A. L. Sandberg. 1988. Identification of C3d receptors on *Candida albicans*. Infect. Immun. 56:252-258.
35. Gilmore, B. J., E. M. Retsinas, J. S. Lorentz, and M. P. Hostetter. 1988. An iC3b receptor on *Candida albicans* structure, function and correlates for pathogenicity. J. Infect. Dis. 157:38-46.
36. Gustafson, K. S., G. M. Vercelloti, C. M. Bendel, and M. K. Hostetter. 1991. Molecular mimicry in *Candida albicans*. Role of an integrin analogue in adhesion of the yeast to human endothelium. J. Clin. Invest. 87:1896-1902.
37. Wadsworth, E., S. C. Prasad, and R. Calderone. 1993. Analysis of mannoproteins from blastoconidia and hyphae of *Candida albicans* with a common epitope recognized by anti-complement receptor type 2 antibodies. Infect. Immun. 61:4675-4681.
38. Bouali, A., R. Robert, G. Tronchin, and J. M. Senet. 1987. Characterization of binding of human fibrinogen to the surface of germ-tubes and mycelium of *Candida albicans*. J. Gen. Microbiol. 133:545-551.
39. Casanova, M., J. L. Lopez-Ribot, C. Monteagudo, A. Llombart-Bosch, R. Sentandreu, and J. P. Martinez. 1992. Identification of a 58-kilodalton cell surface fibrinogen-binding mannoprotein from *Candida albicans*. Infect. Immun. 60:4221-4229.
40. Page, S., and F. C. Odds. 1988. Binding of plasma proteins to *Candida* species in vitro. J. Gen. Microbiol. 134:2693-2702.
41. Bouchara, J. P., G. Tronchin, V. Annaix, R. Robert, and J. M. Senet. 1990. Laminin receptors on *Candida albicans* germ tubes. Infect. Immun. 58:48-54.
42. López-Ribot, J. L., M. Casanova, C. Monteagudo, P. Sepulveda, and J. P. Martinez. 1994. Evidence for the presence of a high-affinity laminin receptor-like molecule in the surface of *Candida albicans* yeast cells. Infect. Immun. 62:742-746.

43. Klotz, S. A. 1990. Adherence of *Candida albicans* to components of the extracellular matrix. FEMS Microbiol. Lett. 68:249-254.
44. Klotz, S. A., and R. D. Maca. 1988. Endothelial cell contraction increases *Candida* adherence to exposed extracellular matrix. Infect. Immun. 56:2495-2498.
45. Klotz, S. A, and R. L. Smith. 1991. A fibronectin receptor on *Candida albicans* mediates adherence of the fungus to extracellular matrix. J. Infect. Dis. 163:604-610.
46. Nègre, E., T. Vogel, A. Levanon, R. Gut, T. J. Walsh, and D. R. Roberts. 1994. The collagen binding domain of fibronectin contains a high affinity binding site for *Candida albicans*. J. Biol. Chem. 269:22039-22045.
47. Jakab, E., M. Paulsson, F. Ascencio, and A. Ljungh. Expression of vitronectin and fibronectin binding by *Candida albicans* yeast cells. APMIS 101: 187-193.
48. Tronchin, G., J. P. Bouchara, R. Robert, and J. M. Senet. 1988. Adherence of *Candida albicans* germ tubes to plastic: ultrastructural and molecular studies of fibrillar adhesins. Infect. Immun. 56:1987-1993.
49. Chaffin, W. L., B. Collins, J. N. Marx, G. T. Cole, and K. J. Morrow. 1993. Characterization of mutant strains of *Candida albicans* deficient in expression of a surface determinant. Infect. Immn. 61:3449-3458.
50. Han, Y., N. van Rooijen, and J. E. Cutler. 1993. Binding of *Candida albicans* yeast cells to mouse politeal lymph node tissue is mediated by macrophages. Infect. Immun. 61:3244-3249.
51. Kanbe, T., Y. Han, B. Redgrave, M. H. Riesselman, and J. E. Cutler. 1993. Evidence that mannans of *Candida albicans* are responsible for adherence of yeast forms to spleen and lymph node tissue. Infect. Immun. 61:2578-2584.
52. Kanbe, T., M. A. Jutila, and J. E. Cutler. 1992. Evidence that *Candida albicans* binds via a unique adhesion system on phagocytic cells in the marginal zone of the mouse spleen. Infect. Immun. 60:1972-1978.
53. Li, R. K., and J. E. Cutler. 1993. Chemical definition of an epitope/adhesin molecule on *Candida albicans*. J. Biol. Chem. 268:18293-18299.
54. Yu, L., K. K. Lee, H. B. Sheth, P. Lane-Bell, G. Srivatava, O. Hindsgaul, W. Paranchych, R. S. Hodges, and R. T. Irvin. 1994. Fimbria-mediated adherence of *Candida albicans* to glycosphingolipid receptors on human buccal epithelial cells. Infect. Immun. 62:2843-2848.
55. Yu, L., K. K. Lee, K. Ens, P. C. Doig, M. R. Carpenter, W. Staddon, R. S. Hodges, W. Paranchych, and R. T. Irvin. 1994. Partial characterization of a *Candida albicans* fimbrial adhesin. Infect. Immun. 62:2834-2842.
56. Critchley, I. A., and L. J. Douglas. 1987. Isolation and partial characterization of an adhesin from *Candida albicans*. J. Gen. Microbiol. 133:629-636.
57. Tosh, F. D., and L. J. Douglas. 1992. Characterization of a fucoside-binding adhesin of *Candida albicans*. Infect. Immun. 60:4734-4739.
58. Martinez, J. P., J. L. López-Ribot, and W. L. Chaffin. 1994. Heterogeneous surface distribution of the fibrinogen binding protein on *Candida albicans*. Infect. Immun. 62:709-712.
59. López-Ribot, J. L., J. P. Martinez, and W. L. Chaffin. 1995. A comparative study on the C3d-receptor and the 58-kilodalton fibrinogen-binding mannoprotein of *Candida albicans*. Infect. Immun. 63:2126-2132.
60. López-Ribot, J. L., D. Gozalvo, P. Sepulveda, M. Casanova, and J. P. Martinez. 1995. Preliminary characterization of the material released to the culture medium by *Candida albicans* yeast and mycelial cells. Antonie van Leeuwenhoek J. of Microbiol. 68:195-201.
61. Casanova, M., and W. L. Chaffin. 1991. Cell wall glycoproteins of *Candida albicans* as released by different methods. J. Gen. Microbiol. 137:1045-1051.
62. Casanova, M., J. L. Lopez-Ribot, J. P. Martinez, and R. Sentandreu. 1992. Characterization of cell wall proteins from yeast and mycelial cells of *Candida albicans* by labelling with biotin: comparison with other techniques. Infect. Immun. 60:4898-4906.
63. Chaffin, W. L., and D. M. Stocco. 1983. Cell wall proteins of *Candida albicans*. Can. J. Microbiol. 29:1438-1444.
64. Pontón, J. and J. M. Jones. 1986. Analysis of cell wall extracts of *Candida albicans* by sodium dodecyl sulfate-polyacrylamide gel electrophoresis and western blot techniques. infect. Immun. 53:565-572.
65. Sundstrom, P. M. and G. E. Kenny. 1984. Enzymatic release of germ tube specific antigens from cell walls of *Candida albicans*. Infect. Immun. 46:609-614.
66. Tronchin, G., J. P. Bouchara, and R. Robert. 1989. Dynamic changes of the cell wall surface of *Candida albicans* associated with germination and adherence. Eur. J. Cell Biol. 50:285-290.
67. Linehan, L., E. Wadsworth, and R. Calderone. 1988. *Candida albicans* C3d receptor isolated by using a monoclonal antibody. Infect. Immun. 56:1981-1986.
68. Saxena, A., and R. A. Calderone. 1990. Purification and characterization of the extracellular C3d-binding protein of *Candida albicans*. Infect. Immun. 58:309-314.
69. Kanbe, T., R. K. Li, E. Wadsworth, R. A. Calderone, and J. E. Cutler. 1991. Evidence for the expression of the C3d receptor of *Candida albicans* in vitro and in vivo obtained by immunofluorescence and immunoelectron microscopy. Infect. Immun. 59:1832-1838.
70. Cortlandt, D. A., J. L. López-Ribot, K. J. Morrow, D. C. Straus, and W. L. Chaffin. Dynamic expression of a cell surface determinant of *Candida albicans*. Mycopathologia. In press.
71. López-Ribot, J. L., D. A. Cortlandt, D. C. Straus, K. J. Morrow, and W. L. Chaffin. Complex interaction between different proteinaceous components within the cell wall structure of *Candida albicans* Mycopathologia. In press.
72. Dedhar, S., K. Jewell, M. Rojiani, and V. Gray. 1992. The receptor for the basement membrane glycoprotein entactin is the integrin $\alpha 3/\beta 1$. J. Biol. Chem. 267:18908-18914.

Romani, L. 1999. Immunity to *Candida albicans*: Th1, Th2 cells and beyond. Curr. Opin. Microbiol. 2:363-7.

Viudes et al, I & I, 2001.

Example 2

Tissue Invasiveness and Non-acidic pH in Human Candidiasis Correlate with "In Vivo" Expression by *C. albicans* of the Carbohydrate Epitope Recognized by a New Monoclonal Antibody 1H4

Invasive candidiasis is a major cause of morbidity and mortality in immunocompromised patients. The morphogenetic conversions between yeast and hyphal growth forms appears to be critical in the pathogenesis of invasive candidiasis and can be regulated by environmental signals such as extracellular pH. We have characterized the epitope recognized by monoclonal antibody 1H4, generated against the 58-Kilodalton cell wall mannoprotein of *Candida albicans* (mp58), and evaluated the expression of its corresponding epitope in *C. albicans* cells cultured under different conditions of pH and temperature, and "in vivo", in a variety of human tissues from patients with superficial and systemic candidiasis. Our results show that 1H4 recognizes a pH-sensitive carbohydrate epitope on the surface of *C. albicans* cells, ant that this epitope is not restricted to mp58, but is shared with other cell wall mannoproteins. Immunohistological findings indicated that expression of the 1H4 epitope on *C. albicans* cells in tissue sections from human candidiasis correlates with tissue invasion and pH of the niche. Thus, the fact that 1H4 epitope expression selectively identifies invasive and potentially aggressive forms of *Candida albicans* supports its potential value in the management of human candidiasis.

Organisms, culture conditions, and preparation of cell wall extracts. *C. albicans* strain 3153A was used in this work. It was maintained on Sabouraud medium containing 2% (w/v) agar. Yeast cells were grown in suspension culture in the medium of Lee et al. at 22° C. (9). Germ tubes were induced from stationary phase yeast cells by incubating at 37° C. in the same medium for 4-6 h. Cell wall extracts were prepared from intact cells (germ tubes) by treatment with β-mercaptoethanol (β-ME) as described before (10). Briefly, germ-tubes were resuspended in alkaline buffer containing 1% (v/v) β-ME and incubated for 45 min at 37° C. with gentle agitation. After treatment, the cells were sedimented, and the supernatant fluid was recovered, dialyzed, and lyophilized (β-ME extract). The total sugar content in the extract was determined calorimetrically with mannose as the standard.

In another series of experiments (agglutination, see below), liquid cultures of *C. albicans* strains 3153A, SC5314 and 412 (11) were obtained by overnight incubation at different temperatures in different media, including yeast peptone dextrose (YPD, 1% w/v yeast extract, 2% w/v peptone, 2% w/v dextrose [US Biological, Swampscott, Mass.]), Lee and RPMI 1640 (Angus Buffers and Chemicals, Niagara Falls, N.Y.) that had been previously adjusted to neutral (pH 6.8-7.2) or acidic (pH 4.0) pH.

Purification of *C. albicans* mp58. For purification of mp58, components in the β-ME were separated by preparative sodium dodecyl sulfate-polyacrylamide gel electrophoresis (SDS-PAGE) under denaturing conditions. Briefly, about 10 mg (based on total sugar content) of the corresponding β-ME extract were applied to a 13 cm wide×20 cm height, 5-15% polyacrylamide slab gradient gel. Prestained molecular weight standards (Gibco-BRL, Life Technologies InC., Gaithersburg, Md.) were run in parallel in a single reference well formed to one side of the resolving gel slab. The transverse section of the gels corresponding to mp58 (as identified by Coomassie staining) were excised, crushed and polypeptide moieties electroeluted (12).

Generation of 1H4 monoclonal antibody (Mab). Two (BALB/c) mice were immunized with 25 μg of mp58 purified by preparative electrophoresis and subsequent electroelution from the gel slice (see above). Immunization protocols consisted of a first injection (using complete Freund's adjuvant), two subsequent booster injections (with incomplete Freund's adjuvant) at three-week intervals, and one final booster injection without adjuvant three days prior to fusion (all injections were subcutaneous). For hybridoma production, mice were sacrificed and their spleens removed aseptically. Antibody secreting cells were isolated and mixed with myeloma cells (NS1) using drop-wise addition of polyethylene glycol. After the fusion, cells were diluted in selective medium and plated at low densities in multiwell tissue culture dishes. Hybridoma cell lines secreting antibodies against *C. albicans* mp58 were screened by ELISA and immunoblot procedures and single-cell subcloned by the limiting dilution method. A hybridoma cell line producing a Mab designated 1H4 (an IgG1 as determined by an isotyping kit, Zymed) was established. Ascitic fluid for this cell line 1H4 was prepared with the corresponding hybridoma in pristane-primed mice.

Immunoblot analysis. For immunoblot, materials present in the *C. albicans* 3153A β-ME extract were separated by SDS-PAGE using precast 4%-15% gradient minigels (Bio-Rad) and transferred to nitrocellulose membranes. After blocking the membranes in Tris-HCl buffer plus 0.9% (w/v) NaCl (TBS) containing 3% BSA (w/v), they were incubated in the presence of Mab 1H4 (diluted 1:1,000 in TBS with 0.05% TWEEN 20 and 1% BSA) or with a rabbit polyclonal antiserum generated against *C. albicans* cell wall extracts (13). Peroxidase-labeled goat anti-mouse or anti-rabbit immunoglobulins (Bio-Rad) were used as secondary antibodies. Colored reactive bands were developed with $H_2O_2$ and 4-chloro-1-napthol as the chromogenic reagent.

Periodate treatment of antigenic preparations reactive with Mab 1H4. To characterize the nature of the epitope recognized by the 1H4 Mab, periodate treatment of the antigenic preparations initially reactive with Mab 1H4 was carried out using a modified ELISA assay (14). Briefly, the β-ME extract or purified mp58 were used to coat selected wells of a microtitre plate (Immulon 2). After overnight incubation, wells were washed 4 times with phosphate buffer saline pH 7.4 (PBS) additioned with 0.05% TWEEN 20. (PBST) Plates were then rinsed with 50 mM sodium acetate buffer (pH 4.5) prior to exposure to periodate. Sets of wells were then exposed to 10 mM sodium m-periodate (Sigma) for 1 hour at room temperature in the dark. The plates were then washed with sodium acetate buffer and aldehyde groups blacked blocked with 1% glycine solution. The plates were then washed 4 times with PBST, and incubated for 1 hour with 200 μl of a 1:1,000 dilution of Mab 1H4 PBST containing 1% BSA. The plate was washed and goat anti-mouse IgG (Bio-Rad) at a 1:2,000 dilution in PBST plus 1% BSA) was added to the wells of the microtiter plate and incubated for 1 hour. After washings as before 200 μl per well of o-phenylenediamine substrate were added, and developed in the dark for 10 min with gentle agitation. Color development was stopped by addition of 100 μl per well of 1M $H_2SO_4$, and the plate was read at 490 nm in a Benchmark microplate reader (Bio-Rad, Hercules, Calif.).

Agglutination experiments. Slide agglutination tests were performed by directly mixing 15 μl of overgrown tissue culture supernatants from the hybridoma secreting Mab 1H4 with 30 μl of yeast cell suspensions (approximately $2\times10^8$ cells/ml). These preparations were mixed for 1 minute at room temperature and agglutination determined by observing for agglutinates by the unaided eye and by low-power bright field microscopy. Agglutination reactions were scored as very strong (+++), strong (++), medium (+), weak (+/−), or no agglutination (−).

Tissues. Twenty-four human tissue samples from patients with mucocutaneous and systemic candidiasis were retrieved from the files of the Department of Pathology, Hospital Clinico Universitario, Valencia. Fourteen samples were obtained during necropsic examination, and nine corresponded to incisional or endoscopic biopsies. These cases have been extensively characterized (15, 16).

Immunohistochemistry. The immunohistochemical study was performed on four-micrometer paraffin-embedded tissue sections by the avidin-biotin immunoperoxidase technique as previously described (15). Endogenous peroxidase activity was blocked by exposing the tissue sections to 0.3% $H_2O_2$ in absolute methanol for 30 minutes. The sequence of incubations was the following: 2% normal horse serum (20 minutes), 1H4 culture supernatant (45 minutes), biotinylated horse anti-mouse IgG (Vector, Burlingame, Calif.) (30 minutes), and avidin-biotin-peroxidase complex (Vector) (45 minutes). The reaction was developed in 0.5 mg/ml 3-3' diaminobenzidine tetrahydrochloride (Sigma, St. Louis, Mo.) and 3 μl/ml 3% $H_2O_2$ in 50 mmol TRIS, pH 7.6. The slides were counterstained with hematoxylin. All incubations were performed at room temperature Antigen retrieval techniques were not applied in any of the cases.

Establishment of a Mab-producing hybridoma and characterization of the Mab 1H4. We established a hybridoma cell line producing a Mab designated 1H4. Mab 1H4 was an IgG1 which was reactive with *C. albicans* cell wall extracts and purified mp58 in ELISA experiments. Immunoblotting experiments indicated that Mab 1H4 recognized mp58 (used to immunize the mice) but also a higher molecular mass polydisperse material present in the cell wall extracts of *C. albicans* (FIG. 6).

Figure 7:
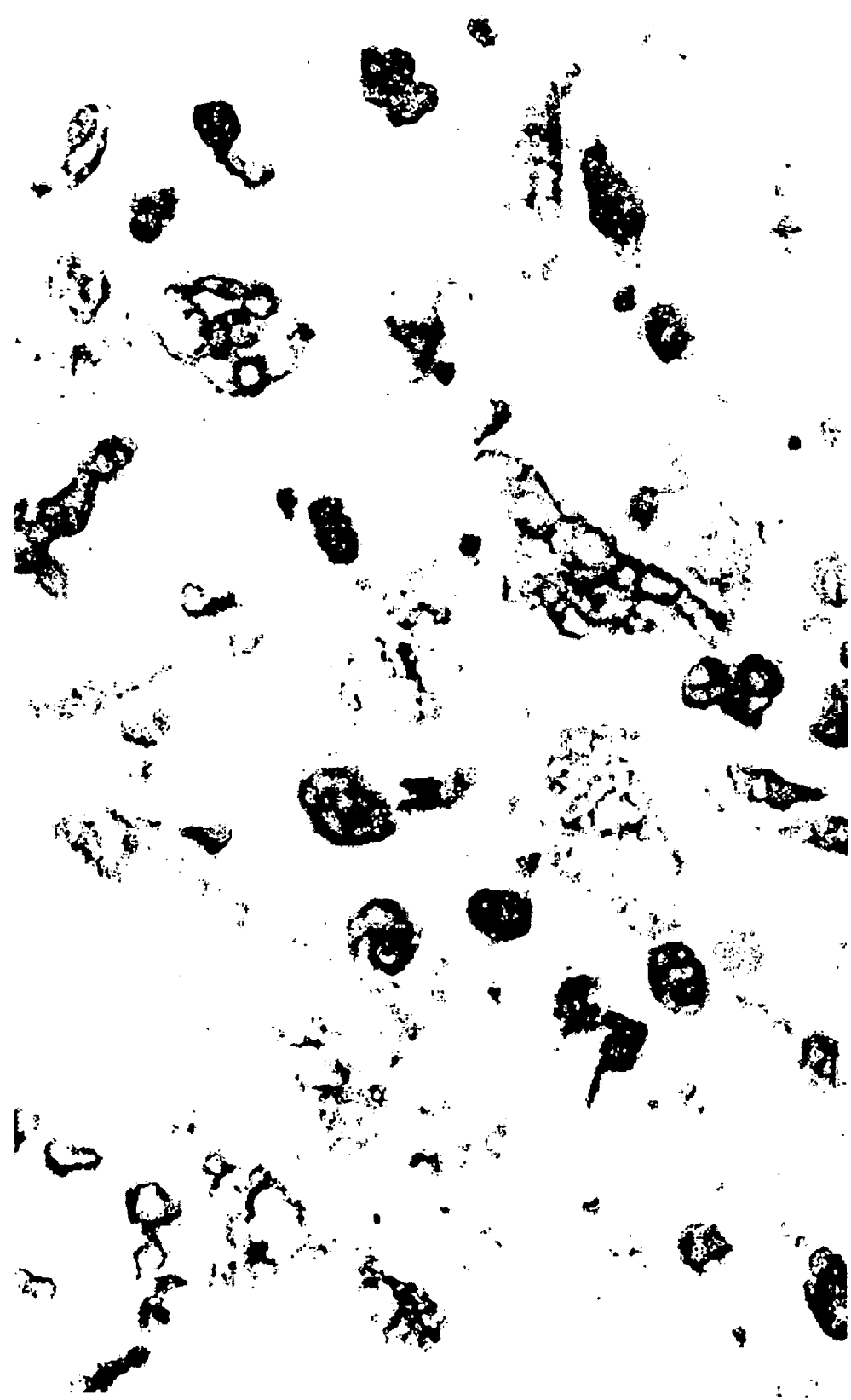

Effects of periodate treatment of antigens reactive with Mab 1H4. *C. albicans* mp58 is a cell surface mannoprotein. Two early observations lead us to believe that the epitope recognized by Mab 1H4 may be of carbohydrate nature. First, in epitope mapping experiments this antibody did not recognize any of the overlapping peptides encompassing the entire sequence of the protein portion of *C. albicans* mp58 (not shown). Second, as shown in FIG. 6, immunoblot analysis with Mab 1H4 demonstrated its cross-reactivity with high molecular mass, highly polydispersed material which represents mainly carbohydrate. As shown in FIG. 7, the antigenic determinants which reacted with the Mab were sensitive to periodate treatment, and 10 mM sodium m-periodate treatment almost completely abolished binding of Mab 1H4 to both mp58 and cell wall extracts. These results indicate that the epitope recognized by Mab 1H4 is of carbohydrate nature.

Expression of the epitope recognized by Mab 1H4 under different in vitro growing conditions: pH dependency. Initial observations established that Mab 1H4 constitutes an agglutinating antibody when *C. albicans* yeast cells are incubated in its presence. We took advantage of this property to further investigate the expression of the epitope recognized by this Mab on the surface of *C. albicans* cells grown under different environmental conditions (growth media and pH). Table I summarizes results from these agglutination experiments with three different *C. albicans* strains grown as yeast cells on YPD at different temperatures and pHs. As indicated in the table, Mab 1H4 agglutinated yeast cells from all strains grown on YPD at different temperatures at neutral pH, but failed to agglutinate those grown under acidic pH. These observations indicated the pH dependency of the expression of the epitope recognized by this Mab. However, this pH dependency is not absolute since the antibody agglutinated (although to a much lesser extent) the same *C. albicans* strains when grown as yeast cells in different media (Lee and RPMI).

TABLE 1

Results of agglutination tests to examine the expression of the epitope recognized by Mab 1H4 on the surface of *C. albicans* (strains 3153A, SC5314 and 412) propagated as yeast forms under different growth conditions.

| Medium | Temperature (° C.) | 3153A Neutral pH | 3153A Acidic pH | SC5314 Neutral pH | SC5314 Acidic pH | 412 Neutral pH | 412 Acidic pH |
|---|---|---|---|---|---|---|---|
| YPD | 24 | ++ | − | +++ | − | + | − |
|  | 30 | ++ | − | +++ | +/− | +++ | − |
|  | 37 | +++ | − | +++ | +/− | +++ | − |
| RPMI | 24 | ++ | + | ++ | ++ | ++ | − |
|  | 30 | + | + | ++ | ++ | + | + |
| Lee | 24 | + | +/− | +++ | ++ | ++ | +/− |

Agglutination reactions were scored as follows:
+++, very strong;
++, strong;
+, medium;
+/−, weak,
−, no agglutination.

Immunohistochemistry in Human Superficial and Systemic Candidiasis

Figure 8:
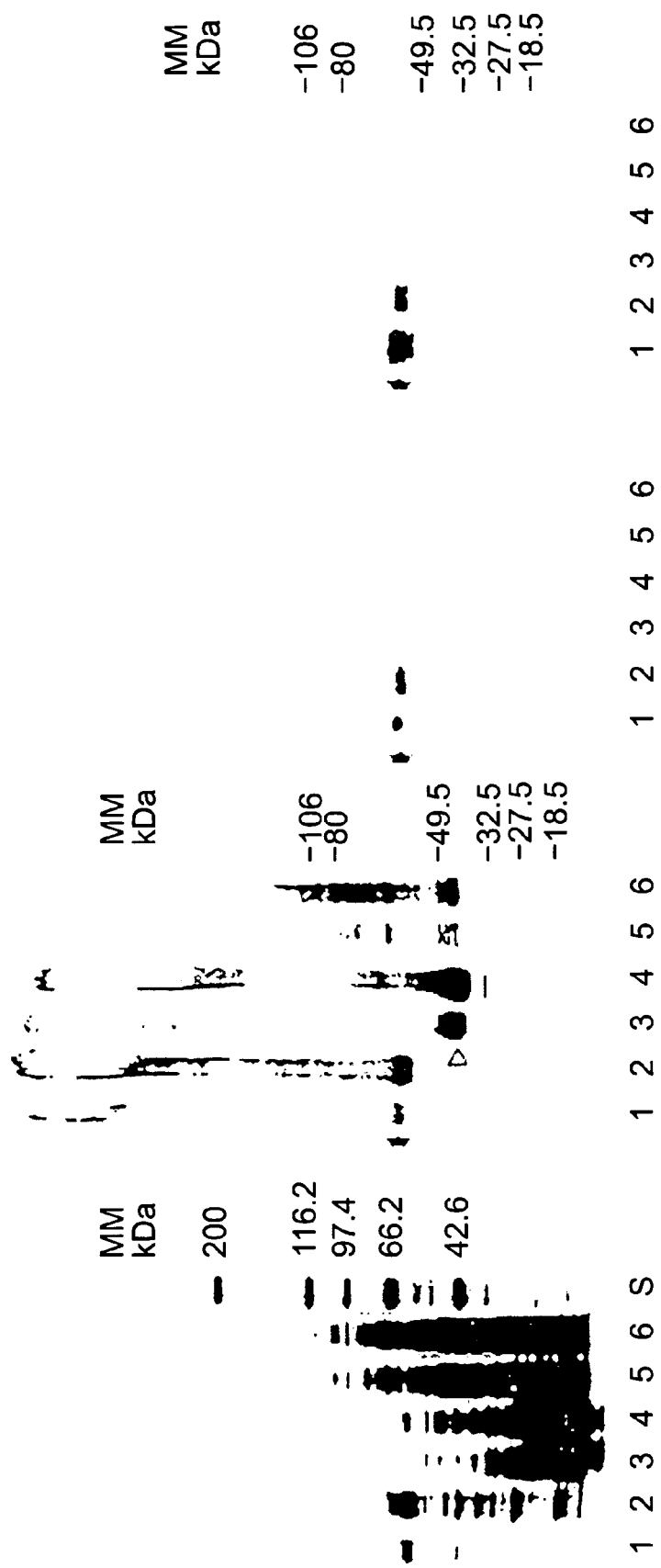
FIGS. 8A-8D illustrate 1H4 immunoreactivity in invasive candidiasis of the esophagus. At low power (A) virtually all *Candida* organisms are labeled; at high power (B) only mycelial cells are present (Immunoperoxidase, hematoxylin counterstain).
Figure 9:
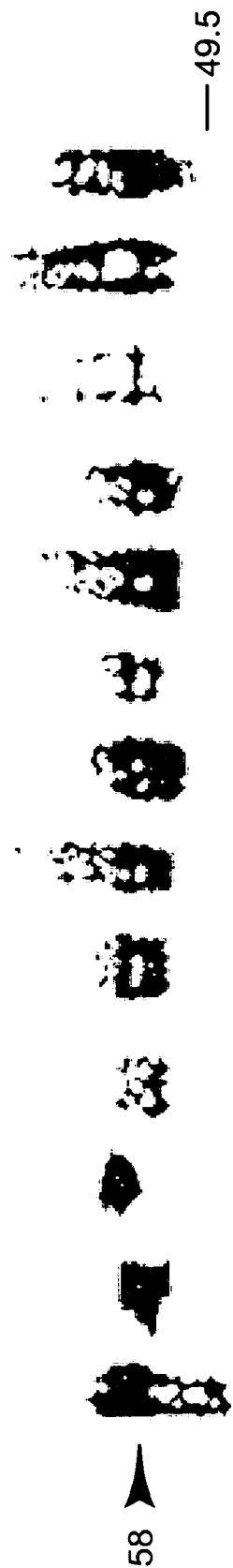
FIG. 9 illustrates 1H4 immunoreactivity of *Candida* organisms in liver (A) and thyroid (B) tissue samples from patients with systemic candidiasis (Immunoperoxidase, hematoxylin counterstain).
Figure 10:
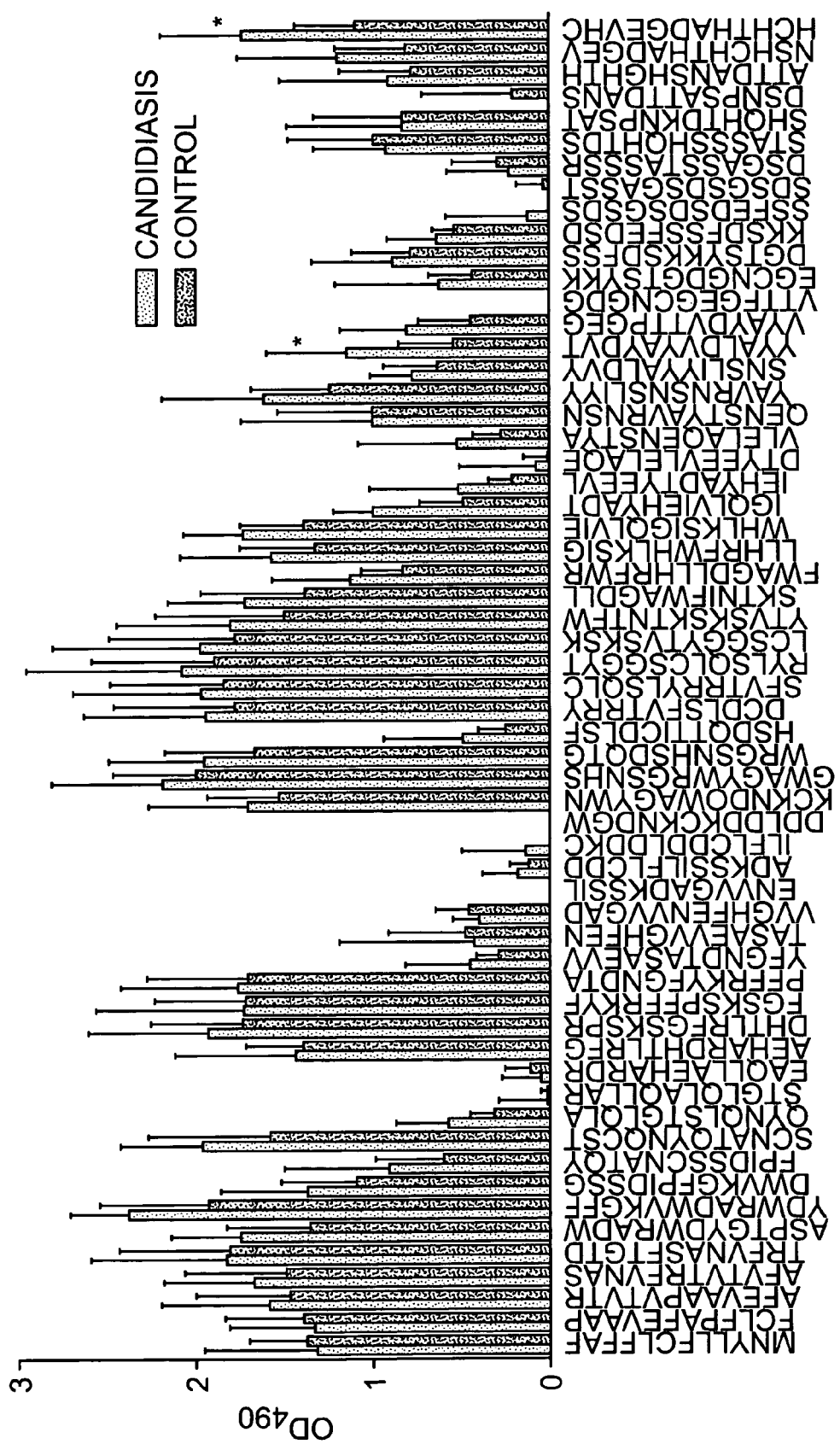
FIG. 10 illustrates both mycelial and yeast cells showing strong 1H4 immunostaining in systemic candidiasis (thyroid tissue, immunoperoxidase, hematoxylin counterstain). The horizontal axis shows the particular peptide detected, and these peptides have sequences, reading from left to right, of SEQ ID NOS 13-71, respectively.

The immunohistochemical results are shown in Table II. In tissue samples from mucosal surfaces with a non-acidic pH such as the tongue, esophagus, intestine, and most skin areas, filamentous forms of *C. albicans* predominated, and most of them exhibited both 1H4 immunostaining and invasive phenotype (FIG. 8). In internal organs having a non-acidic pH (liver, lung, heart, thyroid) from patients with systemic candidiasis, a variable number of yeast cells were found together with hyphae or pseudohyphae in virtually all cases. In these tissues, both yeast and filamentous forms showed strong 1H4 immunoreactivity (FIGS. 9, 10).

In contrast, in those tissues with an acidic pH, such as the stomach and collecting ducts of the kidney, the predominant form of *Candida albicans* cells was the blastospore (yeast). Interestingly, in these locations yeast cells showed no 1H4 immunoreactivity (FIG. 11, A-B). However, when adjacent tissue invasion was present, hyphae or pseudohyphae were the predominant form. A strong 1H4 cell surface immunostaining was seen in most of these filamentous forms of *C. albicans* (FIG. 11, C-D).

In some cases of invasive candidiasis we found 1H4 immunostaining in cellular remnants of degenerated *Candida* organisms within the cytoplasm of phagocytic cells, particularly macrophages (FIG. 12).

TABLE II

Tissue distribution of 1H4 immunoreactivity of *Candida albicans* in human superficial and systemic candidiasis

| Tissue | N° cases | Epithelial surface yeast | Epithelial surface hyphae | Invasive yeast | Invasive hyphae |
|---|---|---|---|---|---|
| skin | 3 | − | − | + | + |
| tongue | 2 | np | + | + | + |
| esophagus | 4 | np | + | + | + |
| stomach | 4 | − | + | +/− | + |
| intestine | 2 | np | + | +/− | + |
| urethra | 1 | +/− | + | + | + |
| kidney | 2 |  |  |  |  |
| glomeruli |  |  |  | + | + |
| tubules |  |  |  | + | + |
| collecting ducts |  |  |  | − | + |

TABLE II-continued

Tissue distribution of 1H4 immunoreactivity of *Candida albicans* in human superficial and systemic candidiasis

| | | 1H4 immunoreactivity | | | |
|---|---|---|---|---|---|
| | | Epithelial surface | | Invasive | |
| Tissue | N° cases | yeast | hyphae | yeast | hyphae |
| bronchus | 1 | − | + | + | + |
| lung | 2 | | | + | + |
| myocardium | 1 | | | + | + |
| thyroid | 1 | | | + | + |
| CNS | 1 | | | + | + |

−, negative;
+, positive;
np, not present

The ability to undergo the yeast to hyphal transition appears to be critical in the pathogenesis of invasive candidiasis (4, 5, 6). Both yeast cells and hyphae are found in infected tissues and contribute to pathogenesis although they may. Yeast cells are better suited for rapid hematogenous dissemination, but together with hyphal elements they are also capable of breaching epithelial and endothelial barriers to cause extensive organ damage (4). During the infectious process yeast cells and hyphae may encounter different microenvironments within the host. At acidic pH, *Candida albicans* grows mostly in the yeast form; at an alkaline pH, it grows primarily in the filamentous form (2, 6, 7). Gastric acid provides an effective barrier to most micro-organisms (normal gastric pH values are 1 to 3.5). In contrast, achlorhydria and the use of H2-antagonists, which raise gastric pH have been found to be associated with higher percentage of invasive gastric candidiasis (17). Similarly, although the skin is relatively inhospitable to fungal growth (18), the experimental increase of skin-surface pH yields more pronounced cutaneous candidiasis in human volunteers (19).

Alkaline-induced filamentation is associated with changes in gene expression. Three genes are known to participate in this alkaline-induced process: PRA1/FBP1, PHR1 and RIM101 (7, 20, 21). Other genes (EFG1, CPH1, TUP1) are involved in non-pH-dependent yeast-to-filament transition (7). The product of PRA1/FBP1 is *C. albicans* mp58, a cell wall mannoprotein which was initially identified by its binding affinity to fibrinogen (21-24). The carbohydrate moiety of mp58 (N- and O-glycosidically linked sugar residues) is known to play an important role in fibrinogen-binding affinity (22). PRA1/FBP1 gene expression is regulated by RIM101 (7), a gene for which a role in host cell damage has been suggested (5). In addition, although the implication of the protein moiety in the immunogenic ability of mp58 has received much attention, a role of the carbohydrate in antigenicity is also expected (25). We have shown that the epitope recognized by 1H4 mAb is of carbohydrate nature, and although it is present in mp58 is not restricted to this glycoprotein but rather shared with other cell wall mannoproteins.

It has been recently hypothesized, regarding fungal infection, that the type of disease and host response depends on the invasiveness of the particular strain of *C. albicans* that is causing the disease (3). Since most strains that cause disease are commensals from the patient, unknown regulatory events are believed to trigger the switch to an invasive state (3). The main virulence factors of *C. albicans* involved in the pathogenesis of candidiasis are: adhesion to host tissues; phase transition, i.e., conversion of yeast cells to filamentous forms; enzymatic activity, and phenotypic switching (3, 26). Morphogenesis of *C. albicans* is a highly complex response of the fungal cells to their environment, with no obligate correlation between strain's ability to form filaments in vivo and in vitro" (6). Moreover, virulence of *C. albicans* is tissue specific (27), and one of the local factors which greatly influence virulence of *Candida* organisms is tissue pH (5, 7, 26, 28). On the other side, immuneprotection against *Candida* infection is also site-specific (26).

Our results support the association of 1H4 epitope, which is in part linked to PRA1/FBP1 gene product in *C. albicans* cell wall, with host cell invasion and tissue damage as well as the pH-dependent phenotype. When gastrointestinal barrier is iatrogenically altered by diagnostic explorations and therapy, particularly in immunodepressed patients, *Candida* organisms produce germ tubes and invade tissues. Here we describe that *C. albicans* cell surface expression of the epitope recognized by mAb 1H4 is significantly increased during invasion. As shown in agglutination experiments using different strains and culture conditions, expression of the 1H4 epitope is not exclusively dependent on pH conditions or phase form of *Candida* organisms. The "in vivo" study shows that it can be detected in filamentous forms in niches with an acidic pH, and in invasive yeast forms in internal organs, but not in non-invading yeast cells. Moreover, since this carbohydrate epitope is part of an immunodominant antigen, a strong immune response towards this molecule is expected during infection (25, 29, 30). This may help contain the infection but also possibly result in increased tissue damage and therefore facilitate dissemination of the remaining organisms. Thus, there seems to be delicate balance between protective immunity and enhanced dissemination. To this end, current experiments in the laboratory are assessing the potential protective role of Mab 1H4 in murine models of systemic candidiasis.

In conclusion, we have generated and characterized a new Mab (1H4) which recognizes a pH-sensitive carbohydrate epitope on the surface of *C. albicans* cells in culture. "In vivo" expression of the 1H4 epitope on the surface of *C. albicans* cells in tissue sections obtained from cases of human candidiasis correlates mainly with tissue invasion, and secondarily with pH of the niche and morphology. Indeed, our data show a strong correlation between invasiveness and expression of this specific epitope, more so than between invasion and morphology. Our findings suggest that this epitope might be involved in promoting persistence and dissemination of *Candida* infection. Moreover, since the expression "in vivo" of the epitope recognized by Mab 1H4 is selectively detected in invasive and potentially aggressive forms of *C. albicans*, this Mab may serve as a useful tool in the management of human candidiasis.

Example 3

Passive Transfer of Protection Experiments with Mab 1H4

Female BALB/c mice, 6 to 7 weeks old were housed in groups in bioclean hoods and provided with water and food ad lib. Six to eight mice were used for each experimental group. Mab 1H4 (approximately 0.6 mg of IgG) was administrated intraperitoneally as ascites two hours before infection. Control animals received the same volume of saline. All mice received an intravenous challenge with $1 \times 10^6$ cells of *C. albicans* clinical strain 412 grown overnight in YEPD at 37° C. (FIG. 13, panel A) or at 24° C. in Lee medium (FIG. 13, panel B). Examination of protective effects of Mab 1H4 was performed by monitoring for survival daily after infection (up to 30 days). Survival data and differences between groups were analyzed using the Kaplan-Meier and logrank tests. P<0.05 was considered statistically significant.

Example 4

Characterization of Anti-mp58 Monoclonal Antibodies

Monoclonal antibodies specific for the mp58 protein were characterized further by ELISA against yeast cell wall extracts.

ELISA Analysis

Immulon 2-HB high-binding 96-well microtiter plates (Dynex) were coated with 1 µg/well of BME cell wall extract of *C. albicans* strains 10261, 26555 or mp58 C-terminal peptide (HTHADGEVH) (SEQ ID NO:11) in 1× PBS, pH 7.4 and incubated for 2 hours at room temperature. All washing steps in ELISAs were performed three times with 1× PBS, 0.05% TWEEN-20® wash buffer. Plates were washed and blocked with a 1% BSA solution at room temperature for 1 hour before hybridoma supernatant samples were added to wells. Plates were incubated with samples and relevant controls such as media alone for one hour at room temperature, washed, and goat anti-mouse IgG-AP (Sigma) diluted 1:5000 in 1× PBS, 0.05% TWEEN-20®, 0.1% BSA was used as a secondary reagent. Plates were developed by addition of 1 mg/ml solution of 4-nitrophenyl phosphate (pNPP) (Sigma), followed by incubation at 37° C. for 30 minutes. Absorbance was read at 405 nm using a SPECTRA-MAX® 190 Plate Reader (Molecular Devices Corp.). Antibody supernatants that had an $OD_{405} \geq 3$ times above background (media alone, ~0.1 OD) were considered positive.

Example 5

Binding of Cloned Anti-mp58 Monoclonal Antibodies to Whole Cell *Candida* Strains These experiments were carried out to determine the reactivity of anti-mp58 mAbs with native mp58 expressed on the surface of *Candida* sp.

Binding to Whole Cell Yeast

Yeast cells (*C. albicans* strain SC5314 and *C. albicans* strain 3153, *C. glabrata, C. guillermondi, C. parapsilosis, C. tropicalis* and *S. cerevisae* X-33 transfected mp58 expression vector) were collected, washed and incubated with antibodies or PBS alone (control) at a concentration of 2 µg/ml after blocking with rabbit IgG (50 µg/ml). Following incubation with antibodies, yeast cells were incubated with Goat-$F_{(ab')2}$-Anti-Mouse-$F_{(ab')2}$-FITC which served as the detection antibody. After antibody labeling, yeast cells were aspirated through the FACScaliber flow cytometer to analyze fluorescence emission (excitation: 488, emission: 570). For each yeast strain, 10,000 events were collected and measured. Units were determined as a percent of the gated positive events by compared to the PBS control.

TABLE 4

Flow Cytometric Analysis

| Strain | C. albicans SC5314 (% of Total) | C. albicans 3153 (% of Total) | C. glabrata (% of Total) | C. guillermondii (% of Total) | C. parapsilosis (% of Total) | C. tropicalis (% of Total) | S. cerevasiae X-33 vector (% of Total) | S. cerevasiae X-33-vector with mp58 gene (% of Total) |
|---|---|---|---|---|---|---|---|---|
| Buffer Control | 1.23 | 0.91 | 0.09 | 0.06 | 0.10 | 0.17 | 0.33 | 0.25 |
| mAb 3C2 | 67.71 | 65.70 | 1.12 | 3.79 | 4.68 | 23.58 | 1.03 | 61.67 |
| mAb 3H3 | ND | 50.02 | 1.27 | 98.53 | 0.82 | 27.69 | 0.72 | 85.98 |

ND = not done

These data indicate that mAbs 3H3 and 3C2 are broadly reactive with mp58 expressed by a number of *Candida* species, including *C. glabrata, C. guillermondii, C. parapsilosis*, and *C. tropicalis*, in addition to *C. albicans*

REFERENCES

The following articles and citations cited with regard to the additional Examples are incorporated into the present application by reference as is set forth herein in their entirety:

1. Odds F C (2000). Pathogenic fungi in the 21st century. Trends Microbiol 8:200-201
2. El Barkani A., Kurzai O, et al. (2000). Dominant active alleles of RIM101 (PRR2) bypass the pH restriction on filamentation of *Candida albicans*. Mol Cell Biol 20:4635-4647.
3. Bernardt J, Herman D, Sheridan M, Calderone R (2001). Adherence and invasion studies of *Candida albicans* strains, using in vitro models of esophageal candidiasis. J Infect Dis 184:1170-1175.
4. Gow N A R, Brown A J P, Odds F C (2002). Fungal morphogenesis and host invasion. Current Opinion Microbiology, 5:366-371.
5. Davis D, Edwards J E Jr, Mitchel A P, Ibrahim A S (2000). *Candida albicans* RIM101 pH response pathway is required for host-pathogen interactions. Infect. Immun 68:5953-5959.

TABLE 3

ELISA Reactivity

| Anti-mp58 mAb | C. albicans 10261 | C. albicans 26555 | mp58 C-terminal Peptide |
|---|---|---|---|
| 3H3 | ++ | ++ | ++ |
| 3C2 | ++ | ++ | ++ |

These results indicate that the 3H3 and 3C2 mAbs recognize native mp58 expressed in the cell wall of *Candida albicans* as well as a synthetic peptide derived from the sequence of the C-terminus of mp58 (amino acids HTHADGEVH) (SEQ ID NO:11).

6. Odds F C, Van Nuffel L, Gow N A R (2000). Survival in experimental *Candida albicans* infections depends on inoculum groth conditions as well as animal host. Microbiology 146:1881-1889.
7. Davis D, Wilson R B, Mitchell A P (2000) RIM101-dependent and independent pathways govern pH responses in *Candida albicans*. Mol. Cell Biol 20:971-978.
8. Mitchel A P (1998). Dimorphism and virulence in *Candida albicans*. Curr Opin Microbiol 1:687-692.
9. Lee K L, Buckley H R, Campbell CC (1975) An amino acid liquid synthetic medium for the development of mycelial and yeast forms of *Candida albicans*. Sabouraudia. 13:148-153.
10. Casanova M, Lopez-Ribot J L, Martinez J P, Sentandreu R (1992) Characterization of cell wall proteins from yeast and mycelial cells of *Candida albicans* by labelling with biotin: comparison with other techniques. Infect. Immun. 60:4898-4906.
11. Lopez-Ribot J L, McAtee R K, Lee L N, Kirkpatrick W R, White T C, Sanglard D, Patterson T F (1998) Distinct patterns of gene expression associated with development of fluconazole resistance in serial *Candida albicans* isolates from human immunodeficiency virus-infected patients with oropharyngeal candidiasis. Antimicrob. Agents Chemother. 42:2932-2937.
12. McDonald C S F, Pappin D, Higgins S (1986) Electroelution of proteins from SDS gels. Trends Genet. 2:35.
13. Lopez-Ribot J L, Chaffin W L (1994). Binding of the extracellular matrix component entactin to *Candida albicans*. Infect. Immun. 62:4564-4571.
14. Woodward M P, Young W W Jr, Bloodgood R A (1985) Detection of monoclonal antibodies specific for carbohydrate epitopes using periodate oxidation. J Immunol Methods 78:143-53.
15. Monteagudo C, Marcilla A, Mormeneo S, Llombart-Bosch A, Sentandreu R. (1995). Specific immunohistochemical identification of *Candida albicans* in paraffin-embedded tissue with a new monoclonal antibody (1B12). Am J Clin Pathol 103:130-135.
16. Monteagudo C, Lopez-Ribot J L, Murgui A, Casanova M, Chaffin W L, Martinez J P (2000). Immunodetection of CD45 epitopes on the surface of *Candida albicans* cells in culture and human infected tissue. Am J Clin Pathol 113: 59-63.
17. Goenka M K, Kochhar R, Chakrabarti A, Kumar A, Gupta O, Talwar P, Mehta S K (1996). *Candida* overgrowth after treatment of duodenal ulcer. A comparison of cimetidine, famotidine, and omeprazole. J Clin Gastroenterol 23:7-10.
18. Wagner D K, Sohnle P (1995) Cutaneous defenses against dermatophytes and yeasts. Clin Microbiol Rev 8:317-335.
19. Runeman B, Faergemann J, Larko O (2000). Experimental *Candida albicans* lesions in healthy humans: dependence on skin pH. Acta Derm Venereol 80:421-424.
20. Saporito-Irwin S M, Birse C E, Sypherd P S, Fonzi W A (1995). PHR1, a pH-regulated gene of *Candida albicans*, is required for morphogenesis. Moll. Cell. Biol. 15:601-613.
21. Sentandreu M, Elorza M V, Sentandreu R, Fonzi W A (1998). Cloning and characterization of PRA1, a gene encoding a novel pH-regulated antigen of *Candida albicans*. J Bacteriol 180:282-289.
22. Casanova M, Lopez-Ribot J L, Monteagudo C, Llombart-Bosch A, Sentandreu R, Martinez J P (1992). Identification of a 58-kilodalton cell surface fibrinogen-binding mannoprotein from *Candida albicans*. Infect Immun 60:4221-4229.
23. Lopez-Ribot J L, Monteagudo C, Sepulveda P, Casanova M, Martinez J P, Chaffin W L J (1996). Expression of the fibrinogen binding mannoprotein and the laminin receptor of *Candida albicans* in vitro and in infected tissues. FEMS Microbiol Lett 142:117-122.
24. Lopez-Ribot J L, Sepulveda P, Cervera A M, Roig D, Gozalbo D, Martinez J P (1997). Cloning of a cDNA fragment encoding part of the protein moiety of the 58-kDa fibrinogen-binding mannoprotein of *Candida albicans*. FEMS Microbiol Lett 157:273-278.
25. Viudes A, Perea S, Lopez-Ribot J L (2001). Identification of continuous B-cell epitopes on the protein moiety of the 58-kilodalton cell wall mannoprotein of *Candida albicans* belonging to a family of immunodominant fungal antigents. Infect Immun 69:2909-2919.
26. Calderone R A, Fonzi W A (2001). Virulence factors of *Candida albicans*. Trends in Microbiology 9:327-335.
27. Taylor B N, Fichtenbaum C, Saavadra M, Slavinski J, Swoboda R, Wozniak K, Arribas A, Powderly W, Fidel P L Jr (2000). In vivo virulence of *Candida albicans* isolates causing mucosal infections in people with the human immunodeficiency virus. J Infect Dis 182:955-959.
28. De Bernardis F, Muhischlegel F A, Cassone A, Fonzi W A (1998). The pH of the host niche controls gene expression in and virulence of *Candida albicans*. Infect Immun 66:3317-3325.
29. Sepulveda P, Lopez-Ribot J L, Murgui A, Canton E, Navarro D, Martinez J P (1998) *Candida albicans* fibrinogen binding protein: expression in clinical strains and immunogeneicity in patients with systemic candidiasis. Int Microbiol 1:209-216.
30. Martinez J P, Gil M L, Lopez-Ribot J L, Chaffin W L (1998). Serologic response to cell wall mannoproteins and proteins of *Candida albicans*. Clin Microbiol Rev 11:121-141.

What is claimed is:

1. A monoclonal antibody produced by the hybridoma cell line deposited at the American Type Culture Collection and that bears the Patent Deposit Designation PTA-8325, wherein the monoclonal antibody is 1H4.

2. The monoclonal antibody according to claim 1, wherein said antibody, upon intraperitoneal pre-administration to mice, confers passive protection, as measured by prolonged survival, against challenge infection with a clinical isolate of *Candida albicans*.

3. The monoclonal antibody according to claim 1, wherein said antibody is suitable for parenteral, oral, intranasal, subcutaneous, aerolized or intravenous administration in a human or animal.

4. Isolated antisera containing the antibody according to claim 1.

5. A diagnostic kit comprising the antibody according to claim 1 and means for detecting binding by said antibody.

6. The diagnostic kit according to claim 5 wherein said means for detecting binding comprises a detectable label that is linked to said antibody.

7. A composition comprising an effective amount of the antibody of claim 1 and a pharmaceutically acceptable vehicle, carrier or excipient.

* * * * *

UNITED STATES PATENT AND TRADEMARK OFFICE
CERTIFICATE OF CORRECTION

PATENT NO.       : 7,632,502 B2                                    Page 1 of 1
APPLICATION NO. : 10/418303
DATED            : December 15, 2009
INVENTOR(S)      : Jose Lopez-Ribot It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1009 days.

Signed and Sealed this

Twenty-first Day of December, 2010

David J. Kappos
*Director of the United States Patent and Trademark Office*

SEQUENCE LISTING

```
<160> NUMBER OF SEQ ID NOS: 12

<210> SEQ ID NO 1
<211> LENGTH: 1596
<212> TYPE: DNA
<213> ORGANISM: Candida albicans
<220> FEATURE:
<221> NAME/KEY: CDS
<222> LOCATION: (569)..(1468)
<223> OTHER INFORMATION:

<400> SEQUENCE: 1
```

-continued

```
acagtttctg tataaacctt agtcaataac ccgatgaaaa taaatgggta aaccttcatt    60
gatgttgtta attttagag agctaccacc aaaaacatat tcagcaaagg ctacctttat   120
attaattatt ccgttttcca agattcctag cggtcgccaa gagaactcaa cactttaacc   180
accatggtat atatcttcat tgctacgggc ccatatattc atgtttccaa ctattctggg   240
caacctcatt ttgtccaaca attttggtga acagttaaaa ttttgcatga aatctttcgc   300
acccacgcac tctcatcaca accactacag ttctatttgc caagagatac cagatgcaag   360
taattaatat attattttct cggtatcttc atggatcagt attccgaaca attcaagaaa   420
agaaagaagg agcgggaaca gttataatgg ttatatctta tgtgttaacc aaagtataaa   480
gaggcaacaa tatctcgttg gaaaagacct ttgtttggtt aatcattttt tttattcaca   540
```

| tctataatca caaactttct ctcgaaat atg aat tat tta ttg ttt tgt tta |      | 592 |
|---|---|---|
|                                    Met Asn Tyr Leu Leu Phe Cys Leu |      |     |
|                                      1               5              |      |     |

| ttt ttt gct ttt tcc gtt gct gca cca gtt acg gtt acc aga ttt gtt | 640 |
|---|---|
| Phe Phe Ala Phe Ser Val Ala Ala Pro Val Thr Val Thr Arg Phe Val |     |
|  10          Ser  15              20                            |     |

| aat gct tca cct aca ggt tac gat tgg cgg gcc gac tgg gtt aaa ggt | 688 |
|---|---|
| Asn Ala Ser Pro Thr Gly Tyr Asp Trp Arg Ala Asp Trp Val Lys Gly |     |
|  25              30              35              40             |     |

| ttt ccg att gat ctg tcg tgt aat gcc aca caa tat aat caa tta tct | 736 |
|---|---|
| Phe Pro Ile Asp Leu Ser Cys Asn Ala Thr Gln Tyr Asn Gln Leu Ser |     |
|              45              50              55                 |     |

| act ggg ttg caa gaa gct caa tta tta gct gaa cat gcc aga gac cac | 784 |
|---|---|
| Thr Gly Leu Gln Glu Ala Gln Leu Leu Ala Glu His Ala Arg Asp His |     |
|          60              65              70                     |     |

| aca ttg aga ttc ggt agc aaa tcg cca ttt ttc aga aaa tac ttt gga | 832 |
|---|---|
| Thr Leu Arg Phe Gly Ser Lys Ser Pro Phe Phe Arg Lys Tyr Phe Gly |     |
|      75              80              85                         |     |

| aat gac act gca agt gct gag gtc gtt ggt cat ttt gaa aat gtt gtc | 880 |
|---|---|
| Asn Asp Thr Ala Ser Ala Glu Val Val Gly His Phe Glu Asn Val Val |     |
|  90              95              100                            |     |

| ggt gct gac aaa tca tcc att ttg ttt ctt tgt gat gac tta gat gat | 928 |
|---|---|
| Gly Ala Asp Lys Ser Ser Ile Leu Phe Leu Cys Asp Asp Leu Asp Asp |     |
| 105             110             115             120             |     |

| aag tgc aaa aat gat ggc tgg gct ggc tat tgg aga ggt tcc aac cat | 976 |
|---|---|
| Lys Cys Lys Asn Asp Gly Trp Ala Gly Tyr Trp Arg Gly Ser Asn His |     |
|             125             130             135                 |     |

| agt gat caa act att att tgt gac tta tct ttt gtt acc aga aga tac | 1024 |
|---|---|
| Ser Asp Gln Thr Ile Ile Cys Asp Leu Ser Phe Val Thr Arg Arg Tyr |      |
|         140             145             150                     |      |

| tta tcc caa cta tgc tcc ggt gga tat acc gtc tcg aaa tct aag aca | 1072 |
|---|---|
| Leu Ser Gln Leu Cys Ser Gly Gly Tyr Thr Val Ser Lys Ser Lys Thr |      |
|     155             160             165                         |      |

| aac att ttt tgg gca ggt gac ttg tta cac aga ttc tgg cac ttg aaa | 1120 |
|---|---|
| Asn Ile Phe Trp Ala Gly Asp Leu Leu His Arg Phe Trp His Leu Lys |      |
| 170             175             180                             |      |

| tcg att ggt caa ctt gtt att gaa cat tac gct gac act tat gag gag | 1168 |
|---|---|
| Ser Ile Gly Gln Leu Val Ile Glu His Tyr Ala Asp Thr Tyr Glu Glu |      |
| 185             190             195             200             |      |

| gtt ctt gaa ttg gct caa gaa aat tca act tat gct gta aga aac tca | 1216 |
|---|---|
| Val Leu Glu Leu Ala Gln Glu Asn Ser Thr Tyr Ala Val Arg Asn Ser |      |
|             205             210             215                 |      |

| aac tca ttg att tat tat gct ttg gat gtg tat gca tat gat gtg aca | 1264 |
|---|---|
| Asn Ser Leu Ile Tyr Tyr Ala Leu Asp Val Tyr Ala Tyr Asp Val Thr |      |
|         220             225             230                     |      |

```
att ccc ggc gaa ggg tgc aat gga gat ggt act ctg tac aag aaa tca      1312
Ile Pro Gly Glu Gly Cys Asn Gly Asp Gly Thr Leu Tyr Lys Lys Ser
        235                 240                 245 gat ttt agc agc ttc gag gat agc gac agt ggc tct gat tca ggg gcc      1360
Asp Phe Ser Ser Phe Glu Asp Ser Asp Ser Gly Ser Asp Ser Gly Ala
250                 255                 260 agt agc aca gcc tca agt tct cat caa cat acc gat agc aac cct agc      1408
Ser Ser Thr Ala Ser Ser Ser His Gln His Thr Asp Ser Asn Pro Ser
265                 270                 275                 280 gcc aca aca gat gct aac ctg cat tgc cac aca cat gca gat ggt gaa      1456
Ala Thr Thr Asp Ala Asn Leu His Cys His Thr His Ala Asp Gly Glu
                285                 290                 295 gtc cac tgt taa ttgttaagtt caggcattaa acaattttta aggtgtttca          1508
Val His Cys tggatatctt tttatagatt gaattaataa gattaattgc aaaatcgctt gtagacaaaa    1568
gagtaatttt catctaaatc tagaattg                                       1596

<210> SEQ ID NO 2
<211> LENGTH: 299
<212> TYPE: PRT
<213> ORGANISM: Candida albicans

<400> SEQUENCE: 2

Met Asn Tyr Leu Leu Phe Cys Leu Phe Phe Ala Phe Ser Val Ala Ala
1               5                   10                  15

Pro Val Thr Val Thr Arg Phe Val Asn Ala Ser Pro Thr Gly Tyr Asp
            20                  25                  30

Trp Arg Ala Asp Trp Val Lys Gly Phe Pro Ile Asp Leu Ser Cys Asn
        35                  40                  45

Ala Thr Gln Tyr Asn Gln Leu Ser Thr Gly Leu Gln Glu Ala Gln Leu
    50                  55                  60

Leu Ala Glu His Ala Arg Asp His Thr Leu Arg Phe Gly Ser Lys Ser
65                  70                  75                  80

Pro Phe Phe Arg Lys Tyr Phe Gly Asn Asp Thr Ala Ser Ala Glu Val
                85                  90                  95

Val Gly His Phe Glu Asn Val Val Gly Ala Asp Lys Ser Ser Ile Leu
            100                 105                 110

Phe Leu Cys Asp Asp Leu Asp Asp Lys Cys Lys Asn Asp Gly Trp Ala
        115                 120                 125

Gly Tyr Trp Arg Gly Ser Asn His Ser Asp Gln Thr Ile Ile Cys Asp
    130                 135                 140

Leu Ser Phe Val Thr Arg Arg Tyr Leu Ser Gln Leu Cys Ser Gly Gly
145                 150                 155                 160

Tyr Thr Val Ser Lys Ser Lys Thr Asn Ile Phe Trp Ala Gly Asp Leu
                165                 170                 175

Leu His Arg Phe Trp His Leu Lys Ser Ile Gly Gln Leu Val Ile Glu
            180                 185                 190

His Tyr Ala Asp Thr Tyr Glu Glu Val Leu Glu Leu Ala Gln Glu Asn
        195                 200                 205

Ser Thr Tyr Ala Val Arg Asn Ser Asn Ser Leu Ile Tyr Tyr Ala Leu
    210                 215                 220

Asp Val Tyr Ala Tyr Asp Val Thr Ile Pro Gly Glu Gly Cys Asn Gly
225                 230                 235                 240

Asp Gly Thr Leu Tyr Lys Lys Ser Asp Phe Ser Ser Phe Glu Asp Ser
                245                 250                 255
```

Asp Ser Gly Ser Asp Ser Gly Ala Ser Ser Thr Ala Ser Ser Ser His
                260                 265                 270

Gln His Thr Asp Ser Asn Pro Ser Ala Thr Thr Asp Ala Asn Leu His
            275                 280                 285

Cys His Thr His Ala Asp Gly Glu Val His Cys
        290                 295

<210> SEQ ID NO 3
<211> LENGTH: 900
<212> TYPE: DNA
<213> ORGANISM: Candida albicans

<400> SEQUENCE: 3
atgaattatt tattgttttg tttattttt gcttttccg ttgctgcacc agttacggtt      60
accagatttg ttaatgcttc acctacaggt tacgattggc gggccgactg ggttaaaggt     120
tttccgattg atctgtcgtg taatgccaca caatataatc aattatctac tgggttgcaa     180
gaagctcaat tattagctga acatgccaga gaccacacat tgagattcgg tagcaaatcg     240
ccatttttca gaaatacttt tggaaatgac actgcaagtg ctgaggtcgt tggtcatttt     300
gaaaatgttg tcggtgctga caaatcatcc attttgtttc tttgtgatga cttagatgat     360
aagtgcaaaa atgatggctg gctggctat tggagaggtt ccaaccatag tgatcaaact      420
attatttgtg acttatcttt tgttaccaga agatacttat cccaactatg ctccggtgga     480
tataccgtct cgaaatctaa gacaaacatt ttttgggcag gtgacttgtt acacagattc     540
tggcacttga aatcgattgg tcaacttgtt attgaacatt acgctgacac ttatgaggag     600
gttcttgaat ggctcaagaa aaattcaact tatgctgtaa gaaactcaaa ctcattgatt     660
tattatgctt tggatgtgta tgcatatgat gtgacaattc ccggcgaagg gtgcaatgga     720
gatggtactc tgtacaagaa atcagatttt agcagcttcg aggatagcga cagtggctct     780
gattcagggg ccagtagcac agcctcaagt tctcatcaac ataccgatag caaccctagc     840
gccacaacag atgctaacct gcattgccac acacatgcag atggtgaagt ccactgttaa     900

<210> SEQ ID NO 4
<211> LENGTH: 35
<212> TYPE: PRT
<213> ORGANISM: Candida albicans

<400> SEQUENCE: 4

Ala Pro Val Thr Val Thr Arg Phe Val Asn Ala Ser Pro Thr Gly Tyr
1               5                   10                  15

Asp Trp Arg Ala Asp Trp Val Lys Gly Phe Pro Ile Asp Ser Ser Cys
            20                  25                  30

Asn Ala Thr
        35

<210> SEQ ID NO 5
<211> LENGTH: 14
<212> TYPE: PRT
<213> ORGANISM: Candida albicans

<400> SEQUENCE: 5

Asn Ser His Cys His Thr His Ala Asp Gly Glu Val His Cys
1               5                   10

<210> SEQ ID NO 6
<211> LENGTH: 27
<212> TYPE: PRT

```
<213> ORGANISM: Candida albicans

<400> SEQUENCE: 6

Ala Glu His Ala Arg Asp His Thr Leu Arg Phe Gly Ser Lys Ser Pro
1               5                   10                  15

Phe Phe Arg Lys Tyr Phe Gly Asn Asp Thr Ala
            20                  25

<210> SEQ ID NO 7
<211> LENGTH: 22
<212> TYPE: PRT
<213> ORGANISM: Candida albicans

<400> SEQUENCE: 7

Lys Cys Lys Asn Asp Gly Trp Ala Gly Tyr Trp Arg Gly Ser Asn His
1               5                   10                  15

Ser Asp Gln Thr Ile Ile
            20

<210> SEQ ID NO 8
<211> LENGTH: 44
<212> TYPE: PRT
<213> ORGANISM: Candida albicans

<400> SEQUENCE: 8

Thr Arg Arg Tyr Leu Ser Gln Leu Cys Ser Gly Gly Tyr Thr Val Ser
1               5                   10                  15

Lys Ser Lys Thr Asn Ile Phe Trp Ala Gly Asp Leu Leu His Arg Phe
            20                  25                  30

Trp His Leu Lys Ser Ile Gly Gln Leu Val Ile Glu
        35                  40

<210> SEQ ID NO 9
<211> LENGTH: 22
<212> TYPE: PRT
<213> ORGANISM: Candida albicans

<400> SEQUENCE: 9

Tyr Ala Val Arg Asn Ser Asn Ser Leu Ile Tyr Tyr Ala Leu Asp Val
1               5                   10                  15

Tyr Ala Tyr Asp Val Thr
            20

<210> SEQ ID NO 10
<211> LENGTH: 10
<212> TYPE: PRT
<213> ORGANISM: Candida albicans

<400> SEQUENCE: 10

His Thr His Ala Asp Gly Glu Val His Cys
1               5                   10

<210> SEQ ID NO 11
<211> LENGTH: 9
<212> TYPE: PRT
<213> ORGANISM: Candida albicans

<400> SEQUENCE: 11

His Thr His Ala Asp Gly Glu Val His
1               5

<210> SEQ ID NO 12
```

-continued

```
<211> LENGTH: 4
<212> TYPE: PRT
<213> ORGANISM: Candida albicans

<400> SEQUENCE: 12

Arg Gly Asp Ser
1
```